United States Patent
Abe et al.

(10) Patent No.: US 10,126,292 B2
(45) Date of Patent: Nov. 13, 2018

(54) BLOOD ANALYZER

(71) Applicant: SYSMEX CORPORATION, Kobe-shi, OT (JP)

(72) Inventors: Masaki Abe, Kobe (JP); Tomohiro Tsuji, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 99 days.

(21) Appl. No.: 14/664,997

(22) Filed: Mar. 23, 2015

(65) Prior Publication Data

US 2015/0276720 A1    Oct. 1, 2015

(30) Foreign Application Priority Data

Mar. 31, 2014  (JP) ................. 2014-071509

(51) Int. Cl.
| | | |
|---|---|---|
| G01N 33/48 | (2006.01) | |
| G01N 33/50 | (2006.01) | |
| G01N 33/569 | (2006.01) | |
| G01N 33/72 | (2006.01) | |
| G01N 33/80 | (2006.01) | |
| G06G 7/58 | (2006.01) | |
| G01N 33/49 | (2006.01) | |
| G01N 15/14 | (2006.01) | |

(52) U.S. Cl.
CPC ... G01N 33/5094 (2013.01); G01N 33/56972 (2013.01); G01N 33/721 (2013.01); G01N 33/80 (2013.01); G01N 15/1459 (2013.01); G01N 33/492 (2013.01); G01N 2800/222 (2013.01); G01N 2800/224 (2013.01)

(58) Field of Classification Search
None
See application file for complete search history.

(56) References Cited

U.S. PATENT DOCUMENTS

| | | |
|---|---|---|
| 8,080,382 B2 | 12/2011 | Ahearn et al. |
| 2005/0002826 A1 | 1/2005 | Oguni et al. |
| 2005/0255001 A1 | 11/2005 | Padmanabhan et al. |
| 2007/0109530 A1 | 5/2007 | Ueno et al. |
| 2009/0069639 A1 | 3/2009 | Linssen et al. |
| 2009/0111118 A1 | 4/2009 | Mylvaganam et al. |
| 2011/0077870 A1 | 3/2011 | Linssen et al. |

FOREIGN PATENT DOCUMENTS

| | | |
|---|---|---|
| EP | 1785720 A2 | 5/2007 |
| EP | 2194383 A1 | 6/2010 |
| EP | 2302377 A2 | 3/2011 |
| JP | H10-319010 A | 12/1998 |
| JP | 2001-086705 A | 3/2001 |
| JP | 2001-269174 A | 10/2001 |
| JP | 2002-122595 A | 4/2002 |
| JP | 2004-184103 A | 7/2004 |
| JP | 2005-024472 A | 1/2005 |
| JP | 2005-037343 A | 2/2005 |
| JP | 2005-221323 A | 8/2005 |
| JP | 2006-145299 A | 6/2006 |
| JP | 2011-502264 A | 1/2011 |
| JP | 2012-122954 A | 6/2012 |
| JP | 2013-145178 A | 7/2013 |
| WO | 2003/085399 A1 | 10/2003 |

OTHER PUBLICATIONS

Laerke Walther Junggreen Have et al.: "Absolute immature platelet count may predict imminent platelet recovery in thrombocytopenic children following chemotherapy", Pediatric Blood & Cancer, vol. 60, No. 7, Feb. 15, 2013, pp. 1198-1203, XP055194222, ISSN: 1545-5009, DOI: 10.1002/pbc.24484.

*Primary Examiner* — Eric S Dejong
(74) *Attorney, Agent, or Firm* — Metrolexis Law Group, PLLC

(57) ABSTRACT

A blood analyzer is provided that comprises: a measurement unit that measures a blood sample and outputs measurement data, a information processing unit that comprises a processor and a memory that stores a program to be executed by the processor to: analyze the measurement data outputted from the measurement unit, generate analysis data on each of blood cell types including red blood cells, white blood cells, and platelets, and generate support information for discriminating a cause of reduction in the number of blood cells of a predetermined type among the blood cell types from the analysis data comprising first analysis data on the predetermined blood cell type and second analysis data on a blood cell type other than the predetermined blood cell type, and an output unit that outputs the support information.

20 Claims, 16 Drawing Sheets

Fig. 10

INCREASED PLATELET DESTRUCTION SCORING INFORMATION 54d-1

| SCORE<br>TARGET ANALYSIS DATA | 0 | 1 | 2 | 3 | WEIGHT |
|---|---|---|---|---|---|
| IMMATURE GRANULOCYTE FRACTION (%) (SECOND ANALYSIS DATA) | 10.0% ≤ IG% | 5.0% ≤ IG% < 10.0% | 1.0% ≤ IG% < 5.0% | IG% < 1.0% | 1 |
| NUMBER OF NEUTROPHILS (/μL) (SECOND ANALYSIS DATA) | Neut# < 1500 | 1500 ≤ Neut# < 2000 | 2000 ≤ Neut# < 2500 | 2500 ≤ Neut# | 1.5 |
| HEMOGLOBIN CONCENTRATION (g/dL) (SECOND ANALYSIS DATA) | Hgb < 10 | 10 ≤ Hgb < 11 | 11 ≤ Hgb < 12 | 12 ≤ Hgb | 2 |
| MEAN CORPUSCULAR VOLUME (fL) (SECOND ANALYSIS DATA) | 100 ≤ MCV | 95 ≤ MCV < 100 | 90 ≤ MCV < 95 | MCV < 90 | 1 |
| NUMBER OF RETICULOCYTES (/μL) (SECOND ANALYSIS DATA) | RET# < 70000 | 70000 ≤ RET# < 85000 | 85000 ≤ RET# < 100000 | 100000 ≤ RET# | 1 |
| NUMBER OF PLATELETS (/μL) (FIRST ANALYSIS DATA) | 100000 ≤ PLT | 50000 ≤ PLT < 100000 | 25000 ≤ PLT < 50000 | PLT < 25000 | 1 |
| IMMATURE PLATELET FRACTION (%) (FIRST ANALYSIS DATA) | IPF% < 10 | 10 ≤ IPF% < 12 | 12 ≤ IPF% < 15 | 15 ≤ IPF% | 3 |
| NUMBER OF MONOCYTES (/μL) (SECOND ANALYSIS DATA) | Mono# < 250 | 250 ≤ Mono# < 500 | 500 ≤ Mono# < 1000 | 1000 ≤ Mono# | 1.2 |

Fig. 11

DECREASED PLATELET PRODUCTION SCORING INFORMATION 54d-2

| SCORE / TARGET ANALYSIS DATA | 0 | 1 | 2 | 3 | WEIGHT |
|---|---|---|---|---|---|
| NUMBER OF NEUTROPHILS (/μL) (SECOND ANALYSIS DATA) | 3000≦Neut# | 2000≦Neut#<3000 | 1500≦Neut#<2000 | Neut#<1500 | 1 |
| NUMBER OF RED BLOOD CELLS (106/μL) (SECOND ANALYSIS DATA) | 280≦RBC# | 280≦RBC#<250 | 250≦RBC#<180 | RBC#<180 | 3 |
| HEMOGLOBIN CONCENTRATION (g/dL) (SECOND ANALYSIS DATA) | 12<Hgb | 11≦Hgb<12 | 10≦Hgb<11 | Hgb<10 | 1.2 |
| MEAN CORPUSCULAR VOLUME (fL) (SECOND ANALYSIS DATA) | MCV<90 | 90≦MCV<95 | 95≦MCV<100 | 100≦MCV | 1.1 |
| NUMBER OF PLATELETS (/μL) (FIRST ANALYSIS DATA) | 100000≦PLT | 50000≦PLT<100000 | 25000≦PLT<50000 | PLT<25000 | 1 |
| IMMATURE PLATELET FRACTION (%) (FIRST ANALYSIS DATA) | 10≦IPF% | 8≦IPF%<10 | 6≦IPF%<8 | IPF%<6 | 2 |

Fig. 12

INCREASED RED-BLOOD-CELL DESTRUCTION SCORING INFORMATION 54d-3

| SCORE<br>TARGET ANALYSIS DATA | 0 | 1 | 2 | 3 | WEIGHT |
|---|---|---|---|---|---|
| MEAN CORPUSCULAR VOLUME MCV (fL) (FIRST ANALYSIS DATA) | MCV<75, 105≦MCV | 75≦MCV<80, 100≦MCV<105 | 80≦MCV<85, 95≦MCV<100 | 85≦MCV<95 | 2 |
| NUMBER OF NEUTROPHILS (/μL) (SECOND ANALYSIS DATA) | Neut#<1000 | 1000≦Neut#<1500 | 1500≦Neut#<2000 | 2000≦Neut# | 1 |
| NUMBER OF RETICULOCYTES RET (/μL) (FIRST ANALYSIS DATA) | RET#<70000 | 70000≦RET#<80000 | 80000≦RET#<100000 | 100000≦RET# | 3 |
| NUMBER OF PLATELETS (/μL) (SECOND ANALYSIS DATA) | PLT<70000 | 70000≦PLT<100000 | 100000≦PLT<150000 | PLT<150000 | 1 |
| INDICATOR OF FRAGMENTED RED BLOOD CELLS FRC# (FIRST ANALYSIS DATA) | FRC<20 | 20≦FRC<50 | 50≦FRC<100 | 100≦FRC | 2 |

Fig. 13

DECREASED RED-BLOOD-CELL PRODUCTION SCORING INFORMATION 54d-4

| SCORE / TARGET ANALYSIS DATA | 0 | 1 | 2 | 3 | WEIGHT |
|---|---|---|---|---|---|
| NUMBER OF NEUTROPHILS (/uL) (SECOND ANALYSIS DATA) | 2500≦Neut# | 2200≦Neut#<2500 | 2000≦Neut#<2200 | Neut#<2000 | 1 |
| NUMBER OF RED BLOOD CELLS (106/uL) (FIRST ANALYSIS DATA) | 280≦RBC# | 280≦RBC#<250 | 250≦RBC#<180 | RBC#<180 | 1.5 |
| NUMBER OF PLATELETS (/uL) (SECOND ANALYSIS DATA) | 120000<PLT | 100000≦PLT<120000 | 70000≦PLT<100000 | PLT<70000 | 1.2 |
| NUMBER OF RETICULOCYTES RET (FIRST ANALYSIS DATA) | 100000≦RET# | 70000≦RET#<100000 | 40000≦RET#<70000 | RET#<40000 | 3 |
| MEAN CORPUSCULAR VOLUME MCV (fL) (FIRST ANALYSIS DATA) | 85≦MCV<95 | 80≦MCV<85, 95≦MCV<100 | 75≦MCV<80, 100≦MCV<105 | MCV<75, 105<MCV | 2 |
| RED BLOOD CELL DISTRIBUTION WIDTH RDW-SD (fL) (FIRST ANALYSIS DATA) | RDW-SD<50 | 50≦RDW-SD<55 | 55≦RDW-SD<60 | 60≦RDW-SD | 1 |

Fig. 14A
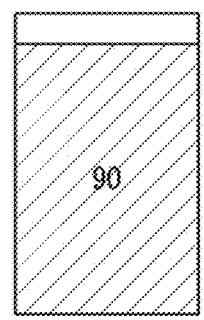
PLATELET REDUCTION /
INCREASED DESTRUCTION
(ITP)
SUSPECT SCORE
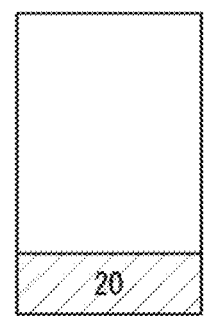
PLATELET REDUCTION /
DECREASED PRODUCTION
(AA/MDS)
SUSPECT SCORE
Fig. 14B
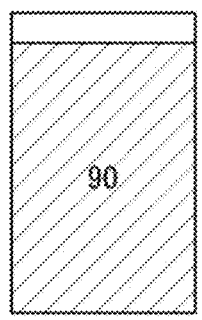
ITP
SUSPECT SCORE
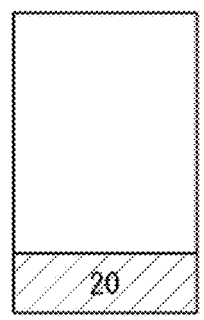
MDS
SUSPECT SCORE
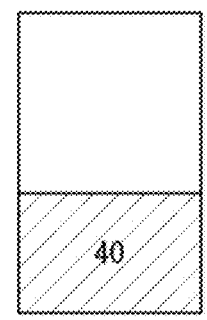
AA
SUSPECT SCORE

BLOOD ANALYZER

CROSS REFERENCE TO RELATED APPLICATION

This application claims priority from prior Japanese Patent Application No. 2014-071509, filed on Mar. 31, 2014, entitled "BLOOD ANALYZER," the entire contents of which are incorporated herein by reference.

BACKGROUND

The disclosure relates to blood analyzers capable of providing information useful in discrimination of cytopenia.

Cytopenia includes thrombocytopenia, erythropenia, leukopenia, and pancytopenia.

In this respect, U.S. Patent Application Publication No. 2005/0002826 states that a percentage of immature platelets is useful information for discrimination between idiopathic thrombocytopenic purpura (ITP) and aplastic anemia (AA), both of which are thrombocytopenia. The measurement apparatus of U.S. Patent Application Publication No. 2005/0002826 is capable of presenting the apparatus user with, as information for discrimination of thrombocytopenia, a percentage of immature platelets obtained from measurement data on platelets.

Note that the percentage of immature platelets=the number of immature platelets/(the number of immature platelets+the number of mature platelets).

However, the technique of U.S. Patent Application Publication No. 2005/0002826 merely presents information on platelets as information for supporting discrimination of thrombocytopenia. A further improvement is desired in the precision of information for supporting discrimination of cytopenia.

SUMMARY

An embodiment relates to a blood analyzer including: a measurement unit that measures a blood sample and outputs measurement data, a information processing unit that comprises a processor and a memory that stores a program to be executed by the processor to: analyze the measurement data outputted from the measurement unit, generate analysis data on each of blood cell types including red blood cells, white blood cells, and platelets, and generate support information for discriminating a cause of reduction in the number of blood cells of a predetermined type among the blood cell types from the analysis data comprising first analysis data on the predetermined blood cell type and second analysis data on a blood cell type other than the predetermined blood cell type, and an output unit that outputs the support information.

Another embodiment relates to a system for improved precision of notifying a physician of a cause in reduction in the number of blood cells of a predetermined type from blood. The system comprises an aspirator that removes fluid from a sample container, a sample preparation unit that has hydraulic pumps and flow paths from a the aspirator to multiple alternative reaction chambers, a detection unit comprising a first detector comprising a diode laser and that generates fluorescence, forward scattering and side scattering signals, a second detector comprising a sheath flow DC detection unit, and a third detector that comprises an SLS-hemoglobin detector wherein each detector is fluidically connected to separate reaction chambers, and an information processing unit comprising a micro-processor and that controls the aspirator, sample preparation unit and detection unit and which receives data from the detection unit, wherein upon activation by a user, the system generates support information for discriminating a cause of reduction in the number of blood cells of a predetermined type among blood cell types including red blood cells, white blood cells and platelets, from data comprising first analysis data on the predetermined blood cell type and second analysis data on a blood cell type other than the predetermined blood cell type.

Still another embodiment relates to a method for facilitating discrimination of a cause of reduction in the number of blood cells of a predetermined type from blood. The method comprises sampling the blood by a sample preparation unit that has multiple alternative reaction chambers, fluidically feeding reacted products to a first detector, a second detector and a third detector from the alternative reaction chambers to produce analysis data for blood cell types including red blood cells, white blood cells, and platelets, and generating support information for discriminating a cause of reduction in the number of blood cells of a predetermined type among the blood cell types from data comprising first analysis data on the predetermined blood cell type and second analysis data on a blood cell type other than the predetermined blood cell type.

BRIEF DESCRIPTION OF DRAWINGS

FIG. 10 is a table for illustrating increased platelet destruction scoring information.

FIG. 11 is a table for illustrating decreased platelet production scoring information.

FIG. 12 is a table for illustrating increased red-blood-cell destruction scoring information.

FIG. 13 is a table for illustrating decreased red-blood-cell production scoring information.

FIGS. 14A and 14B illustrate output examples of discrimination support information on thrombocytopenia.

REPRESENTATIVE EMBODIMENTS

Hereinafter, an embodiment is described in detail with reference to the accompanying drawings.

1. Blood Analyzer

Figure 1:
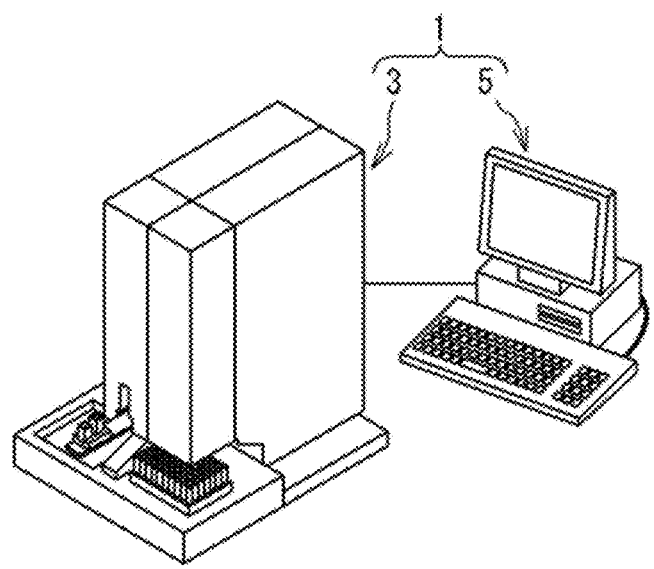
FIG. 1 is a view of a blood analyzer.

FIG. 1 illustrates blood analyzer (multi-parameter blood cell counter) 1. Blood analyzer 1 is configured to count the number of blood cells (white blood cells, red blood cells, platelets) contained in a blood sample for the blood analysis. Blood analyzer 1 includes measurement unit 3 and information processing unit 5 capable of controlling measurement unit 3.

2. Measurement Unit

Figure 2:
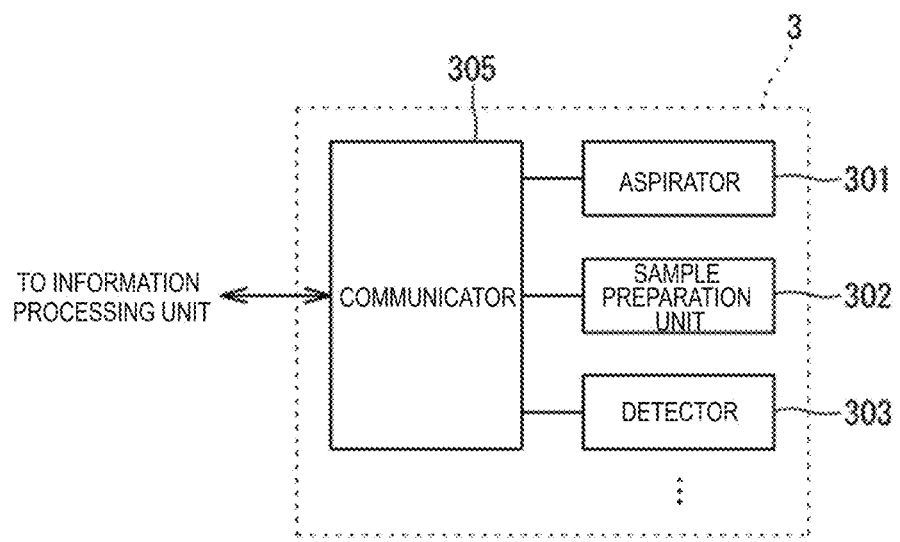
FIG. 2 is a block diagram of a measurement unit.
Figure 3:
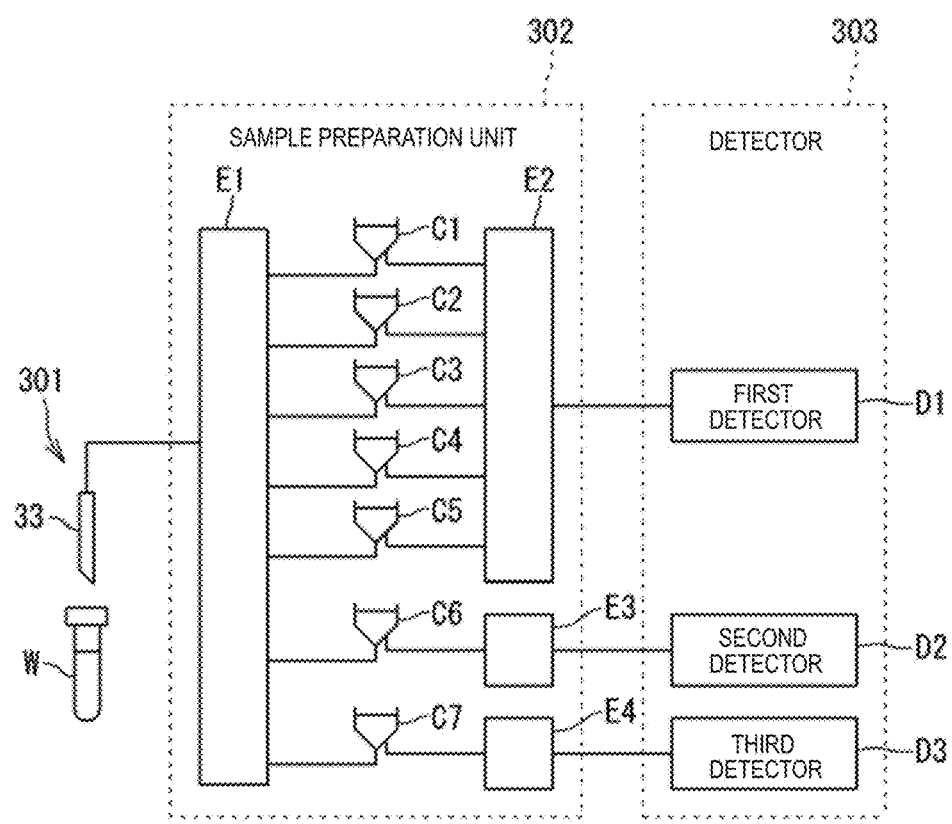
FIG. 3 is a diagram illustrating hydraulic circuits of the measurement unit.

FIGS. 2 and 3 illustrate the configuration of measurement unit 3. Measurement unit 3 includes aspirator 301, sample preparation unit 302, detector 303, communicator 305, and the like. Aspirator 301 is configured to aspirate a blood sample from blood samples stored in sample container W. Aspirator 301 includes piercer 33 configured to aspirate a blood sample in sample container W.

Sample preparation unit 302 is configured to prepare a measurement sample from the blood sample aspirated with aspirator 301, the measurement sample used for measurement. Detector 303 is configured to detect blood cells from the measurement sample prepared by sample preparation unit 302.

Measurement unit 3 communicates with information processing unit 5 through communicator 305. Communicator 305 is configured to receive a control instruction from information processing unit 5. Moreover, communicator 305 is configured to transmit to information processing unit 5 measurement data obtained by detection with detector 303.

Aspirator 301, sample preparation unit 302, and detector 303 are configured to have hydraulic circuits. The hydraulic circuits are configured to operate in such a manner that a measurement sample is prepared from blood aspirated with piercer 33 and the measurement sample is provided to detector 303. Sample preparation unit 302 includes first reaction chamber C1 to seventh reaction chamber C7 configured to prepare a sample. Detector 303 includes first detector D1 to third detector D3 configured to detect a measurement sample.

The hydraulic circuits constituting sample preparation unit 302 include first hydraulic circuit E1 to fourth hydraulic circuit E4. Hydraulic circuits E1 to E4 include unillustrated valves, pumps, and the like, and are configured to switch flow paths with the valves, so that a fluid such as a blood sample can be conveyed into the hydraulic circuits with the pumps. First hydraulic circuit E1 is configured to dispense a blood sample from piercer 33 to each of reaction chambers C1 to C7. Note that first hydraulic circuit E1 is configured to supply reaction chambers C1 to C7 with a diluent, a lysing agent, a staining solution, or the like, as necessary. Liquids such as a diluent, a lysing agent, and a staining solution (sample preparation liquids) are used to prepare a measurement sample.

Second hydraulic circuit E2 is configured to convey, to first detector D1, a measurement sample prepared in first reaction chamber C1 to fifth reaction chamber C5. Third hydraulic circuit E3 is configured to convey a measurement sample prepared in sixth reaction chamber C6 to second detector D2. Fourth hydraulic circuit E4 is configured to convey a measurement sample prepared in seventh reaction chamber C7 to third detector D3. When detection is completed, the measurement samples in detectors D1 to D3 are discharged to a waste fluid chamber (the illustration is omitted).

First reaction chamber C1 is a reaction chamber configured to prepare a sample (first sample) for analysis of white blood cells/nucleated red blood cells.

Second reaction chamber C2 is a reaction chamber configured to prepare a sample (second sample) for analysis of differential white blood cell count.

Third reaction chamber C3 is a reaction chamber configured to prepare a sample (third sample) for analysis of the number of abnormal cells/immature cells.

Fourth reaction chamber C4 is a reaction chamber configured to prepare a sample (fourth sample) for analysis of reticulocytes.

Fifth reaction chamber C5 is a reaction chamber configured to prepare a sample (fifth sample) for analysis of platelets.

Sixth reaction chamber C6 is a reaction chamber configured to prepare a sample (sixth sample) for analysis of red blood cells and platelets.

Seventh reaction chamber C7 is a reaction chamber configured to prepare a sample (seventh sample) for analysis of hemoglobins.

First detector D1 includes a flow cell and an optical detector for a measurement by flow cytometry using a semiconductor laser. The optical detector is configured to detect, as measurement data, optical information (side fluorescence signal, forward scattered light signal, side scattered light signal) from blood cells (such as white blood cells, red blood cells, platelets) in a sample.

First detector D1 is configured to perform a measurement on a first sample (first measurement: measurement for analysis of white blood cells/nucleated red blood cells), a measurement on a second sample (second measurement: measurement for analysis of differential white blood cell count), a measurement on a third sample (third measurement: measurement for analysis of the number of abnormal cells/immature cells), a measurement on a fourth sample (fourth measurement: measurement for analysis of reticulocytes), and a measurement on a fifth sample (fifth measurement: measurement for analysis of platelets).

Second detector D2 is configured to perform a measurement by a sheath flow DC detection method. Second detector D2 is configured to measure a sixth sample (sixth measurement: measurement for analysis of red blood cells and platelets).

Third detector D3 is configured to perform a measurement by an SLS-hemoglobin method. Third detector D3 is configured to measure a seventh sample (seventh measurement: measurement for analysis of hemoglobins).

3. Information Processing Unit

Figure 4:
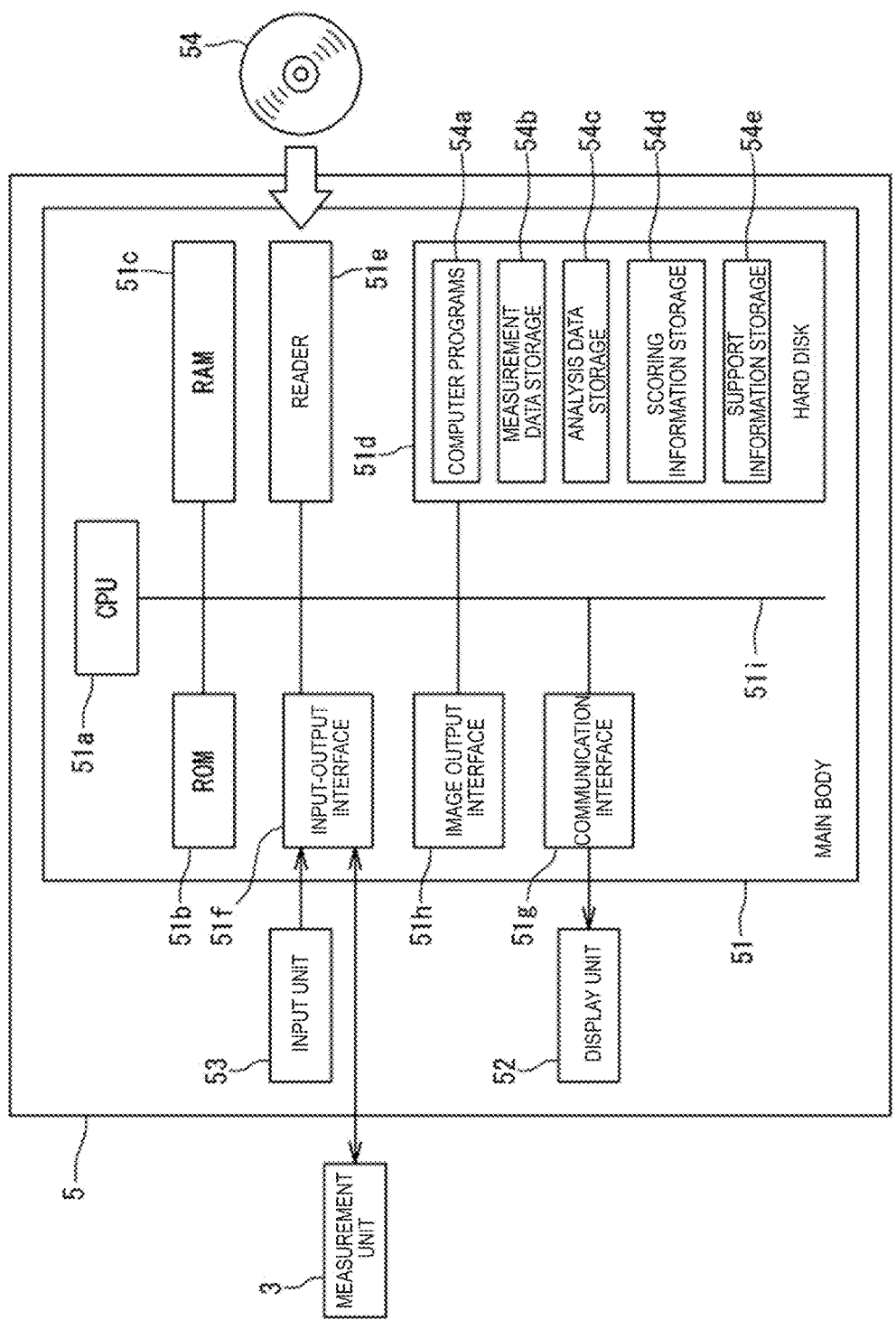
FIG. 4 is a configuration diagram of an information processing unit.

Information processing unit 5 is constituted of a computer. FIG. 4 is a block diagram for illustrating the configuration of information processing unit 5. As illustrated in FIG. 4, computer 5 includes main body (controller) 51, display unit (output unit) 52, and input unit 53. Main body 51 includes CPU 51a, ROM 51b, RAM 51c, hard disk 51d, reader 51e, input-output interface 51f, communication interface 51g, and image output interface 51h. CPU 51a, ROM 51b, RAM 51c, hard disk 51d, reader 51e, input-output interface 51f, communication interface 51g, and image output interface 51h are connected to each other with bus 51i.

CPU 51a is capable of executing computer programs.

Installed in hard disk (memory) 51d are: an operating system and various computer programs 54a executed by CPU 51a, such as application programs, as well as data used for executing the computer programs.

Computer programs 54a include programs for controlling the measurement unit, analyzing measurement data, outputting information, and other processing. Computer programs 54a can be recorded in portable recording medium 54 such as a CD-ROM. Reader 51e is capable of reading computer programs 54a recorded in recording medium 54.

Computer programs 54a can be provided not only with portable recording medium 54 but also through an electric communication line (which may be wired or wireless) from an external device connected to computer 5 with the electric communication line in such a manner as to establish communications therebetween.

Moreover, hard disk 51*d* is configured to function as a storage to store various data (measurement data storage 54*b*, analysis data storage 54*c*, scoring information storage 54*d*, support information storage 54*e*), as well.

Measurement data storage 54*b* is configured to store measurement data received from measurement unit 3. Analysis data storage 54*c* is configured to store analysis data generated by analyzing measurement data. Scoring information storage 54*d* is configured to store information (scoring information) for scoring analysis data. Scoring information storage 54*d* sets the scoring information in advance. Support information storage 54*e* is configured to store support information generated based on analysis data.

Input-output interface 51*f* is connected to measurement unit 3. This enables information processing unit 5 to control measurement unit 3 and to receive measurement data from measurement unit 3.

Image output interface 51*h* is connected to display unit (output unit) 52 constituted of a display and so forth. Thus, information processing unit 5 can display (output) various information such as support information.

Figure 5:
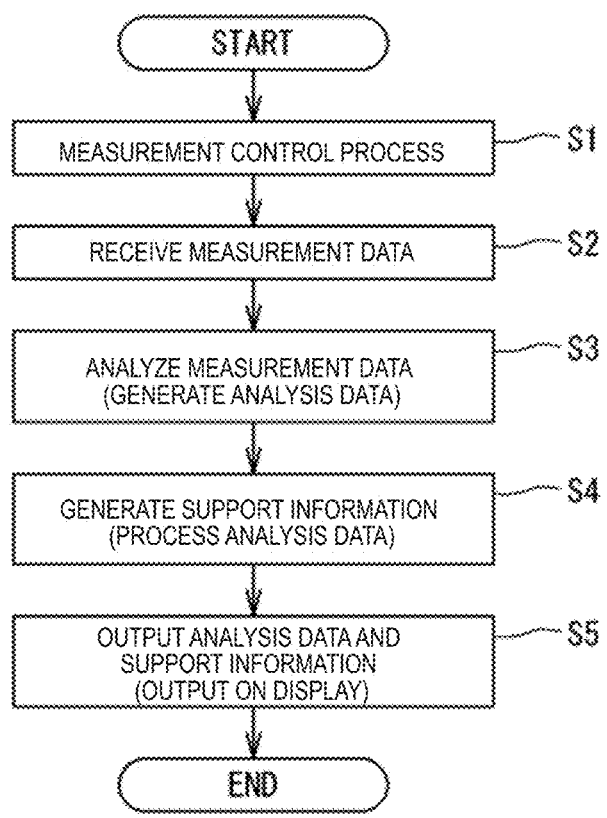
FIG. 5 is a process flowchart of the information processing unit.

FIG. 5 illustrates a measurement-analysis procedure executed by information processing unit 5 (CPU 51*a*). The processes in FIG. 5 are performed by causing CPU 51*a* to execute computer programs 54*a*.

First, information processing unit 5 executes a measurement control process (Step S1). The measurement control process controls measurement unit 3 for measurement of a measurement sample. Measurement unit 3 outputs measurement data obtained by measuring the measurement sample to information processing unit 5. Information processing unit 5 receives the measurement data (Step S2). Subsequently, information processing unit 5 analyzes the measurement data thus received and generates analysis data (Step S3). Information processing unit 5 generates support information, using the analysis data (Step S4). Information processing unit 5 outputs the analysis data and the support information thus generated to display unit (output unit) 52 (Step S5).

Figure 6:
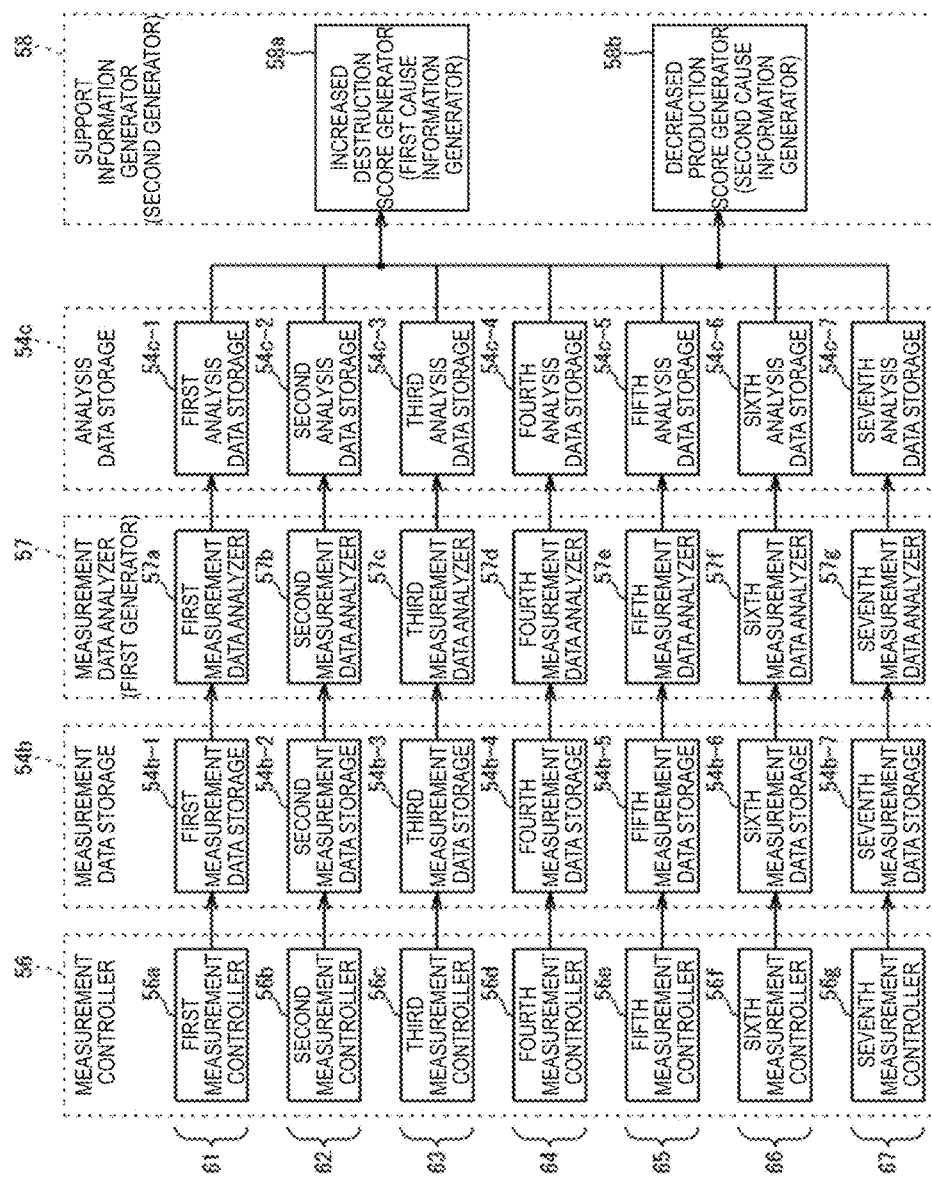
FIG. 6 is a functional block diagram of the information processing unit.

FIG. 6 is a functional block diagram for illustrating functions performed by information processing unit 5 in the process from the measurement control process (Step S1) to the support information generation process (Step S4). The functional block illustrated in FIG. 6 includes measurement controller 56, measurement data storage 54*b*, measurement data analyzer (first generator) 57, analysis data storage 54*c*, and support information generator (second generator) 58. The functions illustrated in the functional block of FIG. 6 are functions performed by information processing unit 5 when CPU 51*a* executes computer programs 54*a*.

Measurement controller 56 is configured to control each measurement in measurement unit 3, and includes first measurement controller 56*a* to seventh measurement controller 56*g*. First measurement controller 56*a* is configured to control a measurement for analysis of white blood cells/nucleated red blood cells (first measurement). Second measurement controller 56*b* is configured to control a measurement for analysis of differential white blood cell count (second measurement). Third measurement controller 56*c* is configured to control a measurement for analysis of the number of abnormal cells/immature cells (third measurement). Fourth measurement controller 56*d* is configured to control a measurement for analysis of reticulocytes (fourth measurement). Fifth measurement controller 56*e* is configured to control a measurement for analysis of platelets (fifth measurement). Sixth measurement controller 56*f* is configured to control a measurement for analysis of red blood cells and platelets (sixth measurement). Seventh measurement controller 56*g* is configured to control a measurement for analysis of hemoglobins (seventh measurement).

Measurement data storage 54*b* is configured to store measurement data received from measurement unit 3, and includes first measurement data storage 54*b*-1 to seventh measurement data storage 54*b*-7.

First measurement data storage 54*b*-1 is configured to store first measurement data (measurement data on white blood cells/nucleated red blood cells) obtained by a measurement for analysis of white blood cells/nucleated red blood cells (first measurement).

Second measurement data storage 54*b*-2 is configured to store second measurement data (measurement data on differential white blood cell count) obtained by a measurement for analysis of differential white blood cell count (second measurement).

Third measurement data storage 54*b*-3 is configured to store third measurement data (measurement data on the number of abnormal cells/immature cells) obtained by a measurement for analysis of the number of abnormal cells/immature cells (third measurement).

Fourth measurement data storage 54*b*-4 is configured to store fourth measurement data (measurement data on reticulocytes) obtained by a measurement for analysis of reticulocytes (fourth measurement).

Fifth measurement data storage 54*b*-5 is configured to store fifth measurement data (measurement data on platelets) obtained by a measurement for analysis of platelets (fifth measurement).

Sixth measurement data storage 54*b*-6 is configured to store sixth measurement data (measurement data on red blood cells and platelets) obtained by a measurement for analysis of red blood cells and platelets (sixth measurement).

Seventh measurement data storage 54*b*-7 is configured to store seventh measurement data (measurement data on hemoglobins) obtained by a measurement for analysis of hemoglobins (seventh measurement).

Measurement data analyzer 57 is configured to generate analysis data using each of measurement data stored in measurement data storages 54*b*-1 to 54*b*-7, and includes first measurement data analyzer 57*a* to seventh measurement data analyzer 57*g*.

First measurement data analyzer 57*a* is configured to generate analysis data on white blood cells/nucleated red blood cells, using first measurement data.

Second measurement data analyzer 57*b* is configured to generate analysis data on differential white blood cell count, using second measurement data.

Third measurement data analyzer 57*c* is configured to generate analysis data on the number of abnormal cells/immature cells, using third measurement data.

Fourth measurement data analyzer 57*d* is configured to generate analysis data on reticulocytes, using fourth measurement data.

Fifth measurement data analyzer 57*e* is configured to generate analysis data on platelets, using fifth measurement data.

Sixth measurement data analyzer 57*f* is configured to generate analysis data on red blood cells and platelets, using sixth measurement data.

Seventh measurement data analyzer 57g is configured to generate analysis data on hemoglobins, using seventh measurement data.

Each of first measurement data analyzer 57a to fifth measurement data analyzer 57e is configured to create a scattergram using optical information (side fluorescence signal, forward scattered light signal, side scattered light signal) that are measurement data outputted from first detector D1. Analyzers 57a to 57e generate analysis data on the number of blood cells and other analysis parameters based on the scattergrams thus created respectively.

Figure 7A:
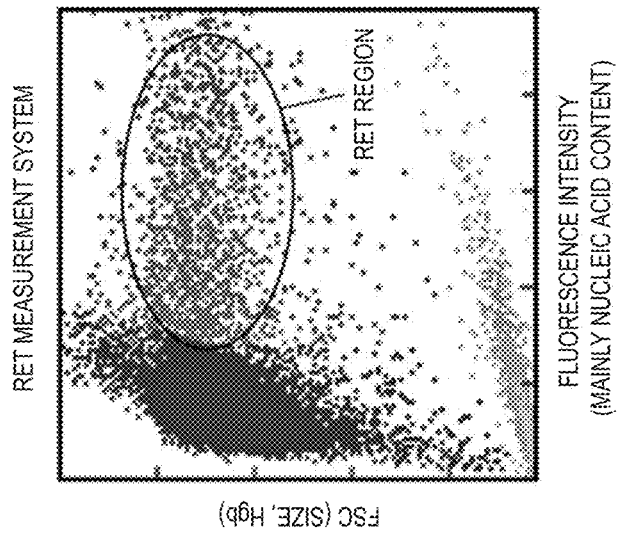
FIG. 7A is a scattergram obtained using a PLT-F measurement system.
Figure 7B:
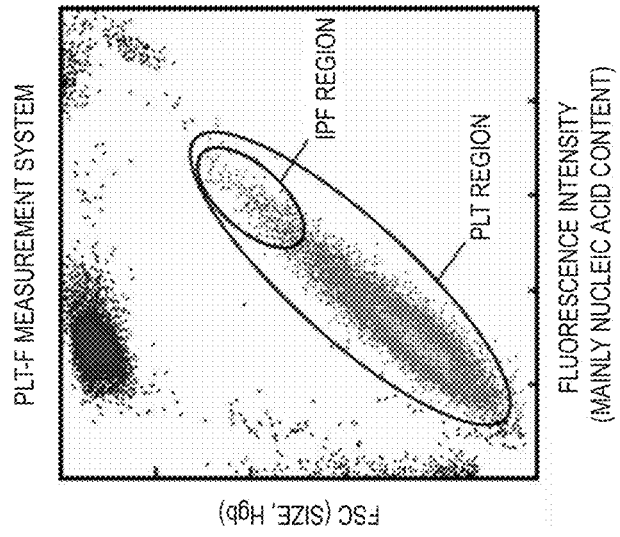
FIG. 7B is a scattergram obtained by an RET measurement system.

As examples of scattergrams created by measurement data analyzers 57a to 57e, FIG. 7A illustrates a scattergram created by fifth measurement data analyzer 57e, and FIG. 7B illustrates a scattergram created by fourth measurement data analyzer 57d.

FIG. 7A illustrates the scattergram in two-dimensional coordinates with (side) fluorescence intensity on the horizontal axis and forward scattered light (FSC) on the vertical axis. The fluorescence intensity and forward scattered light intensity of each particle in a fifth sample are plotted on the coordinates. A region where immature platelets appear (IPF region) and a region where platelets appear (PLT region) are set in the scattergram of FIG. 7A. Fifth measurement data analyzer 57e is configured to count the number of plots appearing in the PLT region (the number of platelets: PLT) and the number of plots appearing in the IPF region (the number of immature platelets: IPF). In this manner, the number of platelets (PLT) and the number of immature platelets (IPF) can be obtained as analysis data on platelets.

Further, fifth measurement data analyzer 57e is configured to generate an immature platelet fraction (IPF %) as analysis data on platelets, using the number of platelets (PLT) and the number of immature platelets (IPF). Note that, here, the immature platelet fraction (IPF %)=the number of immature platelets (IPF)/the number of platelets (PLT).

FIG. 7B illustrates the scattergram in two-dimensional coordinates with (side) fluorescence intensity on the horizontal axis and forward scattered light (FSC) on the vertical axis. The fluorescence intensity and forward scattered light intensity of each particle in a fourth sample are plotted on the coordinates. A region where reticulocytes appear (RET region) is set in the scattergram of FIG. 7B. Fourth measurement data analyzer 57d is configured to count the number of plots appearing in the RET region (the number of reticulocytes: RET#). In this manner, the number of reticulocytes (RET#) can be obtained as analysis data on reticulocytes.

Each of the other measurement data analyzers 57a to 57c configured to analyze measurement data obtained from first detector D1 is also configured to create a scattergram and generate analysis data.

Sixth measurement data analyzer 57f is configured to generate, as analysis data on red blood cells and platelets, analysis data on the number of red blood cells, the number of platelets, and other analysis parameters related to red blood cells and platelets, using sixth measurement data outputted from second detector D2.

Seventh measurement data analyzer 57g is configured to generate analysis data on hemoglobins such as hemoglobin concentration, using seventh measurement data outputted from third detector D3.

Analysis data storage 54c is configured to store analysis data generated by each of measurement data analyzers 57a to 57g, and includes first analysis data storage 54c-1, second analysis data storage 54c-2, third analysis data storage 54c-3, fourth analysis data storage 54c-4, fifth analysis data storage 54c-5, sixth analysis data storage 54c-6, and seventh analysis data storage 54c-7.

As illustrated in FIG. 6, blood analyzer 1 includes analysis channels 61 to 67 for the process from sample measurement to analysis data generation. Channels 61 to 67 includes first analysis channel 61 for analysis of white blood cells/nucleated red blood cells, second analysis channel 62 for analysis of differential white blood cell count, third analysis channel 63 for analysis of the number of abnormal cells/immature cells, fourth analysis channel 64 for analysis of reticulocytes, fifth analysis channel 65 for analysis of platelets, sixth analysis channel 66 for analysis of red blood cells and platelets, and seventh analysis channel 67 for analysis of hemoglobins.

The analysis channels (measurement systems) are independent of each other in terms of analysis data generation. In other words, when analysis data is generated in one analysis channel, measurement data of the analysis channel is used, but no measurement data of the other analysis channels are used. For example, when analysis data on platelets is generated in fifth analysis channel 65 for analysis of platelets, the fifth measurement data analyzer 57e uses only fifth measurement data obtained by measuring a fifth sample, but does not use measurement data in other analysis channels 61 to 64, 66, 67.

4. Analysis Data

Hereinafter, description is given of analysis data generated in each of measurement data analyzers 57a to 57e. Note that analysis data is not limited to data specifically listed below.

Analysis data on white blood cells/nucleated red blood cells include analysis data corresponding to analysis parameters of white blood cells/nucleated red blood cells. Examples of such analysis data corresponding to analysis parameters of white blood cells/nucleated red blood cells include the number of white blood cells (WBC), the number of basophils (BASO), the number of nucleated red blood cells (NRBC#), and the like.

Analysis data on differential white blood cell count include analysis data corresponding to analysis parameters of differential white blood cell count. Examples of such analysis data corresponding to analysis parameters of differential white blood cell count include the number of neutrophils (Neut#), the number of lymphocytes (Lymph#), the number of monocytes (MONO#), the number of eosinophils (EO#), immature granulocyte fraction (IG %), and the like. Note that the immature granulocyte fraction (IG %) is a ratio of the number of immature granulocytes relative to a total leukocyte count.

Analysis data on the number of abnormal cells/immature cells include analysis data corresponding to analysis parameters of the number of abnormal cells/immature cells. Examples of such analysis data corresponding to analysis parameters of the number of abnormal cells/immature cells include the number of white blood cells (WBC-P), a total nucleated cell count (TNC-P), and the like. Note that the total nucleated cell count (TNC-P)=the number of white blood cells+the number of nucleated red blood cells.

Analysis data on reticulocytes include analysis data corresponding to analysis parameters of reticulocytes. Examples of such analysis data corresponding to analysis parameters of reticulocytes include analysis data on as the number of reticulocytes (RET#), fragmented red-blood-cell indicator (FRC#), and the like.

Analysis data on platelets include analysis data corresponding to analysis parameters of platelets. Examples of such analysis data corresponding to analysis parameters of platelets include analysis data on the number of platelets (PLT), immature platelet fraction (IPF %), and the like.

Analysis data on red blood cells and platelets includes analysis data corresponding to analysis parameters of red blood cells and platelets. Examples of such analysis data corresponding to analysis parameters of red blood cells and platelets include analysis data on the number of red blood cells (RBC#), mean corpuscular volume (MCV), red blood cell distribution width (RDW-SD), mean platelet volume (MPV), and the like.

Examples of analysis data on hemoglobin include analysis data on hemoglobin concentration (Hgb) and the like.

5. Discrimination of Cytopenia 5.1 Regarding Cytopenia

Cytopenia is a disease that reduces the number of blood cells in blood. Cytopenia includes thrombocytopenia, erythropenia, leukopenia, and pancytopenia.

Thrombocytopenia reduces the number of platelets in peripheral blood. Examples of the causative disease of thrombocytopenia include idiopathic thrombocytopenic purpura (ITP), aplastic anemia (AA), myelodysplastic syndrome (MDS), and the like. A reduction in the number of platelets in blood is mainly caused by increased destruction and decreased production of platelets. The increased destruction causes idiopathic thrombocytopenic purpura (ITP), while the decreased production causes aplastic anemia (AA) and myelodysplastic syndrome (MDS).

Since the treatment methods are very different between the disease (ITP) caused by the increased destruction and the disease (AA/MDS) caused by the decreased production, the discrimination between these is important. In current clinical settings, cytopenia is not discriminated according to only the result of testing with a blood analyzer, and another testing such as a bone marrow examination is utilized. Particularly, in a case where the decreased production of blood cells in bone marrow is suspected as the cause, bone marrow examination is required. However, a bone marrow examination imposes considerable burdens on patients. Moreover, the test is likely to be conducted more than necessary, too.

Thus, it is desired to readily discriminate the causative disease, and at least it is desired to readily discriminate the cause between the increased destruction and the decreased production which are treated quite differently.

The situation described above is similarly applied to other cytopenias than thrombocytopenia. Examples of the causative disease of erythropenia that reduces the number of red blood cells in peripheral blood include iron-deficiency anemia (IDA), aplastic anemia (AA), myelodysplastic syndrome (MDS), hemolytic anemia (HA), and the like. There are many causes of a reduction in the number of red blood cells in blood, such as iron deficiency in addition to increased destruction and decreased production of red blood cells. The increased destruction causes hemolytic anemia (HA), while the decreased production causes aplastic anemia (AA), myelodysplastic syndrome (MDS), and iron-deficiency anemia (IDA). Further, the cause of iron-deficiency anemia (IDA) also includes iron deficiency.

Thus, it is also desired to readily discriminate the causative disease of erythropenia (and other cytopenias), and at least it is desired to readily discriminate the cause between the increased destruction and decreased production which are treated quite differently.

5.2 Regarding Discrimination of Cytopenia

Figure 8A:
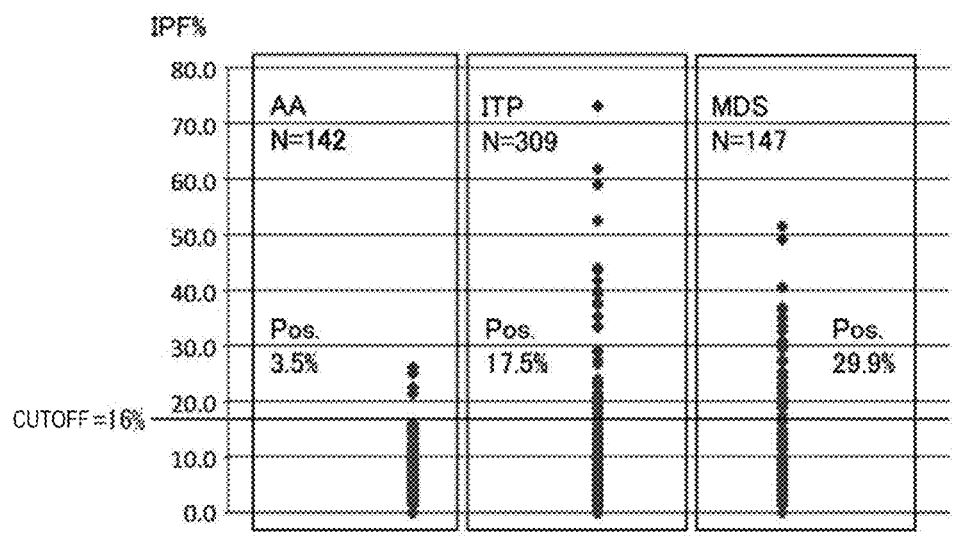
FIG. 8A is a graph for illustrating a relation between diseases and an immature platelet fraction (IPF %)

FIG. 8A illustrates the result of evaluating the cytopenia-discrimination ability using immature platelet fraction (IPF %) similarly to Patent Literature 1. Note that, unlike Patent Literature 1, the disease herein includes myelodysplastic syndrome (MDS) in addition to idiopathic thrombocytopenic purpura (ITP) and aplastic anemia (AA), all of which are thrombocytopenia.

In FIG. 8A, the vertical axis represents the immature platelet fraction (IPF %), and immature platelet fractions of patients with AA, ITP, or MDS are plotted. Note that, in FIG. 8A, the number N of AA cases is 142, the number N of ITP cases is 309, and the number N of MDS cases is 147. In a case where the cutoff value of the immature platelet fraction (IPF %) is set at 16%, the false positive rate of AA is 3.5%, the true positive rate of ITP is 17.5%, and the false positive rate of MDS is 29.9%. Note that the positive means that the immature platelet fraction (IPF %) exceeds the cutoff value.

It can be seen from the result in FIG. 8A that it is not always easy to discriminate between ITP and MDS by using only immature platelet fraction (IPF %).

Figure 8B:
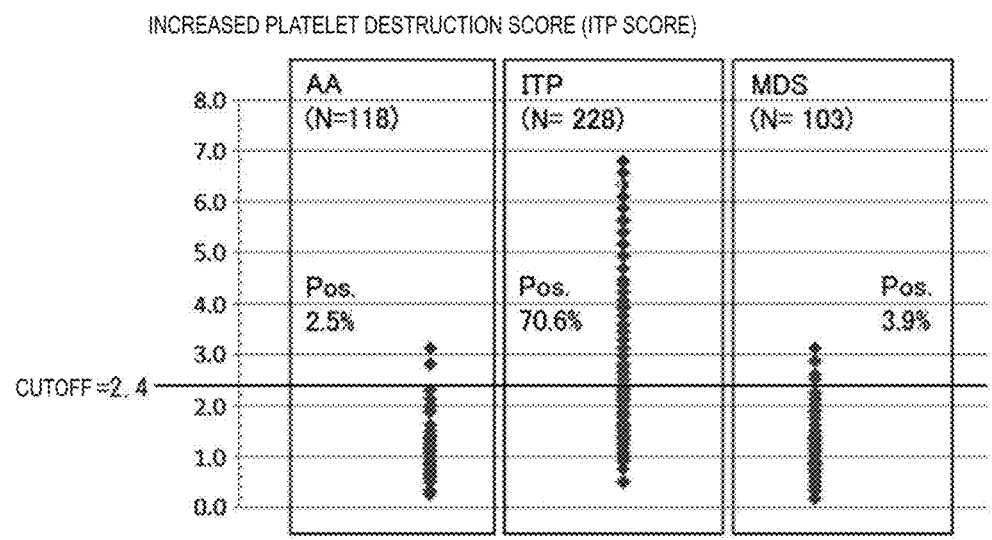
FIG. 8B is a graph for illustrating a relation between the diseases and an ITP score.

Further, the inventors have independently calculated increased platelet destruction scores (ITP scores) by scoring not only the immature platelet fraction (IPF %) but also other parameters, and evaluated the thrombocytopenia-discrimination ability using the ITP scores. FIG. 8B illustrates the result.

Note that the ITP score calculation herein uses: the number of lymphocytes (Lymph#), the number of neutrophils (Neut#), red blood cell distribution width (RDW-SD), hemoglobin concentration (Hgb), the number of reticulocytes (RET#), mean corpuscular volume (MCV), the number of platelets (PLT), mean platelet volume (MPV), immature platelet fraction (IPF %), and the like.

In FIG. 8B, the vertical axis represents the ITP score, and ITP scores of patients with AA, ITP, or MDS are plotted. Note that, in FIG. 8B, the number N of AA cases is 118, the number N of ITP cases is 228, and the number N of MDS cases is 103. The cutoff value of the ITP score is set at 2.4. In this case, the false positive rate of AA is 2.5%; hence, the false positive rate is decreased by 1.0% in comparison with the case of using only the immature platelet fraction. The true positive rate of ITP is 70.6%; hence, the true positive rate is increased by 53.1% in comparison with the case of using only the immature platelet fraction. The false positive rate of MDS is 3.9%; hence, the false positive rate is decreased by 20.0% in comparison with the case of using only the immature platelet fraction.

From the above results, the inventors have obtained the knowledge that in a case of providing information for supporting discrimination of a cause of a reduction in the number of blood cells of a predetermined type (platelet in FIGS. 8A and 8B), information reflecting not only information (immature platelet fraction in FIGS. 8A and 8B) on the predetermined blood cell type but also information on blood cell types other than the predetermined blood cell type enable an improvement in the precision of information presented from blood analyzer 1, and are helpful in discrimination by a physician.

Thus, blood analyzer 1 of the present embodiment does not use analysis data on platelets solely as information for supporting discrimination of thrombocytopenia as in Patent Literature 1, but integrates analysis data on blood cell types and generates support information.

6. Generation of Cytopenia Discrimination Support Information 6.1 Support Information The present embodiment employs, mainly, increased destruction and decreased production of blood cells as the cause of a reduction in the number of the blood cells, the cause being a target of discrimination support by support information outputted from blood analyzer 1. Nevertheless, the cause of a reduction in the number of the blood cells being the target of discrimination support by support information is not limited to the increased destruction and the decreased production, and may be a deficiency in a substance (such as iron, vitamin B12, or folic acid), a deficiency in a hematopoietic factor (such as erythropoietin), bleeding, or the like.

Moreover, the cause of a reduction in the number of the blood cells being the target of discrimination support by support information may be a disease such as ITP, AA, or MDS.

The support information preferably is constituted of cause information data corresponding to causes of a reduction in the number of blood cells being the target of the discrimination support. For example, in the case of discrimination between the increased destruction and the decreased production, the support information is preferably constituted of first cause information on the increased destruction (information indicating a state suspected of the increased destruction) and second cause information on the decreased production (information indicating a state suspected of the decreased production). Instead of using a single indicator for support information for discriminating causes, presenting support information constituted of various information respectively corresponding to the causes enables an improvement in the precision and facilitates discrimination by a physician.

Moreover, the support information may be constituted of first cause information on ITP (information indicating an ITP suspected state), second cause information on MDS (information indicating an MDS suspected state), and third cause information on AA (information indicating an AA suspected state).

6.2 Analysis Data Used to Generate Support Information

In the present embodiment, the analysis data used to generate the support information for discrimination of cytopenia are analysis data on blood cell types. In the present embodiment, from the viewpoint of improving the precision of the support information, analysis data on three blood cell types of white blood cell, red blood cell, and platelet are used to generate the support information. Nevertheless, analysis data on two blood cell types (for example, platelet and red blood cell) may be used.

For one type of blood cells, analysis data are preferably used to generate the support information from the viewpoint of improving the information precision. Nonetheless, one analysis datum or sub-set of data may be used for one type of blood cells.

Among the analysis data used to generate the support information for discrimination of cytopenia, analysis data on white blood cells is preferably one analysis datum or sub-set of data selected from the group consisting of analysis data on the number of abnormal cells/immature cells (analysis data generated from the third channel), analysis data on differential white blood cell count (analysis data generated from the second channel), analysis data on white blood cells/nucleated red blood cells (analysis data generated from the first channel), more preferably one datum or sub-set of analysis data selected from the group consisting of immature granulocyte fraction (IG %), the number of neutrophils (Neut#), the number of monocytes (MONO#), and the number of lymphocytes (Lymph#).

Among the analysis data used to generate the support information for discrimination of cytopenia, analysis data on red blood cells is preferably one datum or sub-set of analysis data selected from the group consisting of analysis data on reticulocytes (analysis data generated from the fourth channel), analysis data on red blood cells and platelets (analysis data generated from the sixth channel), and analysis data on hemoglobins (analysis data generated from the seventh channel), more preferably one datum or sub-set of data selected from the group consisting of hemoglobin concentration (Hgb), mean corpuscular volume (MCV), the number of reticulocytes (RET#), the number of red blood cells (RBC#), red blood cell distribution width (RDW-SD), and fragmented red-blood-cell indicator (FRC#).

Among the analysis data used to generate the support information for discrimination of cytopenia, analysis data on platelets is preferably one datum or sub-set of analysis data selected from the group consisting of analysis data on reticulocytes (analysis data generated from the fourth channel), analysis data on platelets (analysis data generated from the fifth channel), and analysis data on red blood cells and platelets (analysis data generated from the sixth channel), more preferably one datum or sub-set of analysis data selected from the group consisting of the number of platelets (PLT), immature platelet fraction (IPF %), and mean platelet volume (MPV).

In a case of supporting discrimination of a cause of thrombocytopenia (in a case where the predetermined blood cell type is platelet), the information used to generate the support information should include at least analysis data on the predetermined blood cell type (platelet) (first analysis data), and also includes analysis data on another blood cell type (red blood cell or white blood cell) (second analysis data).

In a case of supporting discrimination of a cause of erythropenia (in a case where the predetermined blood cell type is red blood cell), the information used to generate the support information should include at least analysis data on the predetermined blood cell type (red blood cell) (first analysis data), and also includes analysis data on another blood cell type (platelet or white blood cells) (second analysis data).

In a case of supporting discrimination of a cause of leukopenia (in a case where the predetermined blood cell type is white blood cell), the information used to generate the support information should include at least analysis data on the predetermined blood cell type (white blood cells) (first analysis data), and also includes analysis data on another blood cell type (red blood cell or platelet) (second analysis data).

In a case of generating support information (cause information) on thrombocytopenia (in the case where the predetermined blood cell type is platelet), the analysis data on the predetermined blood cell type (platelet) (first analysis data) preferably includes at least immature platelet fraction (IPF %). This is because increased platelet destruction (ITP) tends to increase the immature platelet fraction.

Meanwhile, in a case of decreased platelet production (AA/MDS), the immature platelet fraction is low for AA in many cases, and distributed in a wide range for MDS. Thus, in a case of generating both of first cause information on the increased platelet destruction (information indicating a state suspected of the increased destruction) and second cause information on the decreased platelet production (information indicating a state suspected of the decreased production), importance should be placed on the immature platelet fraction more when the first cause information on the increased platelet destruction is generated.

In the case of generating support information (cause information) on thrombocytopenia (in the case where the predetermined blood cell type is platelet), the analysis data (second analysis data) on a first blood cell type (red blood cell) other than the predetermined blood cell type preferably includes hemoglobin concentration (Hgb). This is because decreased platelet production (AA/MDS) tends to decrease the hemoglobin concentration; meanwhile, in the case of increased platelet destruction (ITP), the hemoglobin concentration tends to be normal.

In the case of generating support information (cause information) on thrombocytopenia (in the case where the predetermined blood cell type is platelet), the analysis data (second analysis data) on the first blood cell type (red blood cell) other than the predetermined blood cell type preferably includes the number of red blood cells (RBC#). This is because decreased platelet production (AA/MDS) tends to decrease the number of red blood cells; meanwhile, in the case of increased platelet destruction (ITP), the number of red blood cells tends to be normal.

In the case of generating support information (cause information) on thrombocytopenia (in the case where the predetermined blood cell type is platelet), the analysis data (second analysis data) on the first blood cell type (red blood cell) other than the predetermined blood cell type preferably includes mean corpuscular volume (MCV). This is because red blood cells may also become abnormal in the case of decreased platelet production, but the mean corpuscular volume is likely to be outside the normal range.

In the case of generating support information (cause information) on thrombocytopenia (in the case where the predetermined blood cell type is platelet), the analysis data (second analysis data) on a second blood cell type (white blood cell) other than the predetermined blood cell type preferably includes the number of neutrophils (Neut#). This is because decreased platelet production (AA/MDS) tends to decrease the number of neutrophils; meanwhile, in the case of increased platelet destruction (ITP), the number of neutrophils tends to be normal.

In the case of generating support information (cause information) on thrombocytopenia (in the case where the predetermined blood cell type is platelet), the analysis data (second analysis data) on the second blood cell type (white blood cell) other than the predetermined blood cell type preferably includes the number of monocytes (MONO#). This is because decreased platelet production (AA) tends to decrease the number of monocytes; meanwhile, in the case of increased platelet destruction (ITP), the number of neutrophils tends to be normal.

From the above, in a case of generating the support information on the increased platelet destruction (first cause information) (in the case where the predetermined blood cell type is platelet), the analysis data (second analysis data) on the second blood cell type (white blood cell) other than the predetermined blood cell type preferably includes one datum or sub-set of analysis data selected from the group consisting of the number of neutrophils (Neut#) and the number of monocytes (MONO#). Moreover, in the case of generating the support information on the increased platelet destruction (first cause information) (in the case where the predetermined blood cell type is platelet), the analysis data (second analysis data) on the first blood cell type (red blood cell) other than the predetermined blood cell type preferably includes hemoglobin concentration (Hgb).

Further, in a case of generating the support information on the decreased platelet production (second cause information) (in the case where the predetermined blood cell type is platelet), the analysis data (second analysis data) on the second blood cell type (white blood cell) other than the predetermined blood cell type preferably includes the number of neutrophils (Neut#). Moreover, in the case of generating the support information on the decreased platelet production (second cause information) (in the case where the predetermined blood cell type is platelet), the analysis data (second analysis data) on the first blood cell type (red blood cell) other than the predetermined blood cell type preferably includes one datum or sub-set of analysis data selected from the group consisting of the number of red blood cells (RBC#), hemoglobin concentration (Hgb), and mean corpuscular volume (MCV).

In a case of generating support information (cause information) on erythropenia (in the case where the predetermined blood cell type is red blood cell), the analysis data on the predetermined blood cell type (red blood cell) (first analysis data) preferably includes the number of reticulocytes (RET#). This is because, in a case of increased red-blood-cell destruction, the production is increased to compensate for the amount destroyed (consumed), consequently increasing the number of reticulocytes; meanwhile, in a case of decreased red-blood-cell production, red blood cells are hardly produced, so that the number of reticulocytes tends to be small.

In the case of generating support information (cause information) on erythropenia (in the case where the predetermined blood cell type is red blood cell), the analysis data on the predetermined blood cell type (red blood cell) (first analysis data) preferably includes mean corpuscular volume (MCV). This is because, in the case of decreased red-blood-cell production, the mean corpuscular volume is likely to be outside the normal range due to the abnormality of the red blood cells; meanwhile, in the case of increased red-blood-cell destruction, the red blood cell is abnormal only to a lesser degree, so that the mean corpuscular volume tends to be near the normal range.

In the case of generating support information (cause information) on erythropenia (in the case where the predetermined blood cell type is red blood cell), the analysis data on the predetermined blood cell type (red blood cell) (first analysis data) preferably includes fragmented red-blood-cell indicator (FRC#). This is because increased red-blood-cell destruction tends to increase fragments (fragmented red blood cells) resulting from the red blood cell destruction.

In the case of generating support information (cause information) on erythropenia (in the case where the predetermined blood cell type is red blood cell), the analysis data on the predetermined blood cell type (red blood cell) (first analysis data) preferably includes the number of red blood cells (RBC#). This is because serious anemia is likely to occur in the case of decreased red-blood-cell production (AA/MDS).

In the case of generating support information (cause information) on erythropenia (in the case where the predetermined blood cell type is red blood cell), the analysis data on the predetermined blood cell type (red blood cell) (first analysis data) preferably includes red blood cell distribution width (RDW-SD). This is because the state of red blood cell production varies in the case of decreased red-blood-cell production (AA/MDS).

In the case of generating support information (cause information) on erythropenia (in the case where the predetermined blood cell type is red blood cell), the analysis data (second analysis data) on a first blood cell type (white blood cell) other than the predetermined blood cell type preferably includes the number of neutrophils (Neut#); in addition, the second analysis data (analysis data) on platelets preferably includes the number of platelets (PLT). This is because the number of neutrophils and the number of platelets suggest decreased production (AA/MDS) in some cases.

From the above, in a case of generating support information on the increased red-blood-cell destruction (first cause information) (in the case where the predetermined blood cell type is red blood cell), the analysis data on the predetermined blood cell type (red blood cell) (first analysis data) preferably includes one datum or sub-set of analysis data selected from the group consisting of mean corpuscular volume (MCV), the number of reticulocytes (RET#), and fragmented red-blood-cell indicator (FRC#).

Moreover, in the case of generating the support information on the increased red-blood-cell destruction (first cause information) (in the case where the predetermined blood cell type is red blood cell), the second analysis data preferably includes one datum or subset of analysis data selected from the group consisting of the number of neutrophils (Neut#) and the number of platelets (PLT).

Further, in a case of generating support information on the decreased red-blood-cell production (second cause information) (in the case where the predetermined blood cell type is red blood cell), the analysis data on the predetermined blood cell type (red blood cell) (first analysis data) preferably includes one datum or sub-set of analysis data selected from the group consisting of the number of red blood cells (RBC#), the number of reticulocytes (RET#), mean corpuscular volume (MCV), and red blood cell distribution width (RDW-SD).

Moreover, in the case of generating the support information on the decreased red-blood-cell production (second cause information) (in the case where the predetermined blood cell type is red blood cell), the second analysis data preferably includes one datum or sub-set of analysis data selected from the group consisting of the number of neutrophils (Neut#) and the number of platelets (PLT).

6.3 Generation of Thrombocytopenia Discrimination Support Information

Figure 9:
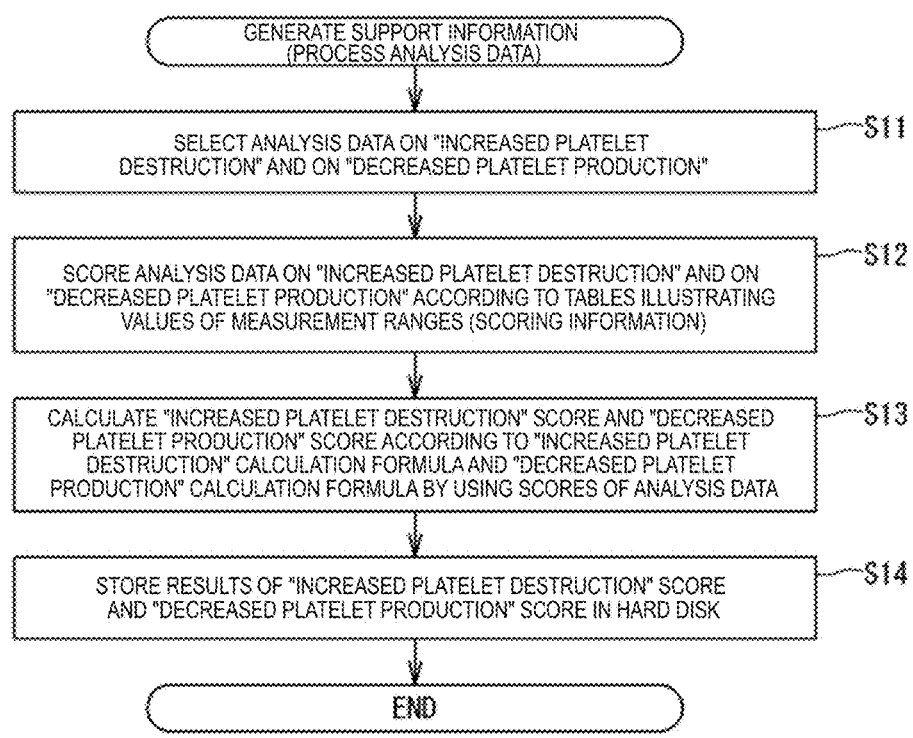
FIG. 9 is a flowchart for illustrating a support information generation step.

FIG. 9 illustrates a process procedure of the support information generation step (Step S4) in FIG. 5. Note that support information generator (second generator) 58 in FIG. 6 corresponds to a function unit configured to execute this support information generation step. Support information generator 58 in FIG. 6 includes increased destruction score generator (first cause information generator) 58a configured to generate discrimination support information on increased destruction of blood cells (first cause information) and decreased blood-cell production score generator (second cause information generator) 58b.

Increased destruction score generator 58a and decreased production score generator 58b are each configured to generate discrimination support information from analysis data stored in analysis data storage 54c, by referring to scoring information (information for support information generation) stored in scoring information storage 54d.

Scoring information storage 54d is configured to store increased platelet destruction scoring information 54d-1 (see FIG. 10) that are information for generating discrimination support information on increased platelet destruction, and decreased platelet production scoring information 54d-2 (see FIG. 11) that are information for generating discrimination support information on decreased platelet production.

Note that scoring information storage 54d is configured to store information 54d-3 and 54d-4 (see FIGS. 12, 13) for generating discrimination support information on erythropenia to be described later, too. These information 54d-3 and 54-4 are described later.

To generate discrimination support information on thrombocytopenia, increased destruction score generator 58a selects analysis data (first target analysis data) used to generate discrimination support information on increased platelet destruction (first cause information) among the analysis data stored in analysis data storage 54c, by referring to increased platelet destruction scoring information 54d-1 (Step S11).

Set in increased platelet destruction scoring information 54d-1 are first target analysis data on increased platelet destruction including: immature granulocyte fraction (IG %), the number of neutrophils (Neut#), hemoglobin concentration (Hgb), mean corpuscular volume (MCV), the number of reticulocytes (RET#), the number of platelets (PLT), immature platelet fraction (IPF %), and the number of monocytes (MONO#). Increased destruction score generator 58a reads these first target analysis data from analysis data storage 54c.

Similarly, decreased production score generator 58b selects analysis data (second target analysis data) used to generate discrimination support information on decreased platelet production (second cause information) among the analysis data stored in analysis data storage 54c, by referring to decreased platelet production scoring information 54d-2 (Step S11).

Set in decreased platelet production scoring information 54d-2 are second target analysis data on decreased platelet production including: the number of neutrophils (Neut#), the number of red blood cells (RBC#), hemoglobin concentration (Hgb), mean corpuscular volume (MCV), the number of platelets (PLT), and immature platelet fraction (IPF %). Decreased production score generator 58b reads these second target analysis data from analysis data storage 54c.

As described above, in the present embodiment, analysis channels (measurement systems) 61 to 67 are independent of each other in terms of analysis data generation. When analysis data is generated in one analysis channel, measurement data of the analysis channel is used, but no measurement data of the other analysis channels are used.

On the other hand, when discrimination support information on cytopenia is generated (in the case where the predetermined blood cell type is platelet), the present embodiment uses analysis data on the first blood cell type (red blood cell) and analysis data on the second blood cell type (white blood cell) other than analysis data on the predetermined blood cell type (platelet).

Specifically, when discrimination support information on thrombocytopenia is generated, used are not only analysis data generated in fifth analysis channel 65 where analysis data on the predetermined blood cell type (platelet) (for example, immature platelet fraction (IPF %)) is generated, but also analysis data generated in another analysis channel (such as second analysis channel 62, fourth analysis channel 64, sixth analysis channel 66, seventh analysis channel 67). In this manner, in the present embodiment, analysis data in the analysis channels (measurement systems) are transversely used in generating the support information.

Subsequently, increased destruction score generator 58a scores (normalizes) values of first target analysis data according to increased platelet destruction scoring information (table illustrating values of measurement ranges) 54d-1 illustrated in FIG. 10.

Increased platelet destruction scoring information (table illustrating values of measurement ranges) 54d-1 defines correspondences between values of first target analysis data and scores (0 to 3). Increased destruction score generator 58a converts the value of each first target analysis data into a score (first score) according to scoring information 54d-1 (Step S12).

Similarly, decreased production score generator 58b scores (normalizes) values of second target analysis data according to decreased platelet production scoring information (table illustrating values of measurement ranges) 54d-2 illustrated in FIG. 11.

Decreased platelet production scoring information (table illustrating values of measurement ranges) 54d-2 also defines correspondences between values of second target analysis data and scores (0 to 3). Decreased production score generator 58b converts the value of each second target analysis data into a score (second score) according to scoring information 54d-2 (Step S12).

Scoring as described above facilitates support information generation with analysis data integrated. The present embodiment comprehensively considers analysis data on blood cell types (platelet, red blood cell, white blood cell). However, the analysis data include values in totally different units, accordingly making it difficult to comprehensively consider the analysis data if the values thereof are unchanged. In contrast, setting scoring information 54d-1 to 54d-4 in advance as in the present embodiment and scoring analysis data according to the scoring information make it possible to calculate scores using simple calculation formulas as described later.

Then, increased destruction score generator 58a assigns a weight to the first score of each first target analysis data according to the importance characterizing the increased destruction state (i.e., multiplies the first scores by weights), sums up the weighted first scores, and divides the sum by the number of the first target analysis data to thus obtain an increased platelet destruction score (discrimination support information: first cause information) (Step S13). Note that the weight of each target analysis data is also set in scoring information 54d-1.

Moreover, in a case where a value of first target analysis data matches a first special condition clearly indicative of the characteristic in the increased destruction state, an increased destruction score may be obtained by adding a value set according to the first special condition to the increased destruction score obtained as described above.

Further, the step may omit the operation of dividing the sum of the weighted first scores by the number of the first target analysis data.

Similarly, decreased production score generator 58b assigns a weight to the second score of each second target analysis data according to the importance characterizing the decreased production state (i.e., multiplies the second scores by weights), sums up the weighted second scores, and divides the sum by the number of the second target analysis data to thus obtain a decreased platelet production score (discrimination support information: second cause information) (Step S13). Note that the weight of each target analysis data is also set in scoring information 54d-2.

Moreover, in a case where a value of second target analysis data matches a second special condition clearly indicative of the characteristic in the decreased production state, a decreased production score may be obtained by adding a value set according to the second special condition to the decreased production score obtained as described above.

Further, the step may omit the operation of dividing the sum of the weighted second scores by the number of the second target analysis data.

The calculation formula for the scores calculated as described above is as follows.

$$B_{all} = A_1 \times B_1 + A_2 \times B_2 + A_3 \times B_3 + \ldots + A_n \times B_n$$

$$C = B_{all} \div n$$

$$\text{Score } E = C + (D_1 + D_2 + \ldots + D_m)$$

Note that, in the case of omitting the division operation, score E is calculated according a formula: $E = B_{all} + (D_1 + D_2 + \ldots + D_m)$.

Here, n: the number of target analysis data $A_i$: a score of target analysis data (i: 1 to n)

$B_i$: a weight (i: 1 to n)

$D_j$: a value added according to special condition $X_j$ (j: 1 to m: m is the number of special conditions)

As the first special condition of the increased destruction, for example, the following two conditions $X_1$, $X_2$ can be set:

$X_1$: $D_1=15$ with an immature platelet fraction (IPF %)>10%; otherwise, $D_1=0$, and $X_2$: $D_2=40$ with a hemoglobin concentration (Hgb)<12.0 g/dl and the number of neutrophils (Neut#)>2000/uL; otherwise, $D_2=0$.

As the second special condition of the decreased production, for example, the following two conditions $X_1$, $X_2$ can be set:

X1: $D_1=20$ with an immature platelet fraction (IPF %)<6%; otherwise, $D_1=0$; and X2: $D_2=10$ with a hemoglobin concentration (Hgb)<10.0 g/dl and the number of neutrophils (Neut#)<1500; otherwise, $D_2=0$.

According to the calculation formula, if the first target analysis data on the increased destruction are as illustrated in FIG. 10, the increased destruction score is obtained according to the following calculation formula.

$B_{all}$=[score of immature granulocyte fraction (IG %)×1]+[score of the number of neutrophils (Neut#)×1.5]+[score of hemoglobin concentration (Hgb)×2]+[score of mean corpuscular volume (MCV)×1]+[score of the number of reticulocytes (RET#)×1]+[score of the number of platelets (PLT)×1]+[score of immature platelet fraction (IPF %)×3]+[score of the number of monocytes (MONO#)×1.2]

$C = B_{all} \div 8$

Increased destruction score=$C+(D_1+D_2)$

Moreover, if the second target analysis data on the decreased production are as illustrated in FIG. 11, the decreased production score is obtained according to the following calculation formula.

$B_{all}$=[score of the number of neutrophils (Neut#)×1]+[score of the number of red blood cells (RBC#)×3]+[score of hemoglobin concentration (Hgb)×1.2]+[score of mean corpuscular volume (MCV)×1.1]+[score of the number of platelets (PLT)×1]+[score of immature platelet fraction (IPF %)×2]

$C = B_{all} \div 6$

Decreased production score=$C+(D_1+D_2)$

Note that the weight of the immature platelet fraction in the calculation formula for the increased destruction score is 3 whereas the weight of the immature platelet fraction in the calculation formula for the decreased production score is 2.

Importance is placed on the immature platelet fraction more in the increased destruction score calculation.

Support information storage 54e of hard disk 51d stores, as support information, the increased destruction score and the decreased production score of platelets calculated as described above (Step S14).

The discrimination ability of the increased destruction score obtained by the above calculation formula for the increased destruction score is evaluated on 227 cases of the disease (ITP) in the increased destruction state and on 221 cases of the disease (AA/MDS) in which the destruction is not increased. In a case where the cutoff value of the increased destruction score obtained by the above calculation formula for the increased destruction score is 1.8, the positive rate of the former (ITP) is 73.6%, while the positive rate of the latter (AA/MDS) is 14.5%. Note that the positive means that a score exceeds the cutoff value, while negative means that a score is less than the cutoff value.

Moreover, the discrimination ability of the decreased production score obtained by the above calculation formula for the decreased production score is evaluated on the 221 cases of the disease (AA/MDS) in the decreased production state and on the 227 cases of the disease (ITP) in which the production is not decreased. In a case where the cutoff value of the decreased production score obtained by the above calculation formula for the decreased production score is 1.4, the positive rate of the former (AA/MDS) is 86.4%, while the positive rate of the latter (ITP) is 18.1%. Note that the positive means that a score exceeds the cutoff value, while negative means that a score is less than the cutoff value.

It can be seen from the above that the increased destruction score and the decreased production score favorably exhibit a state suspected of the increased destruction and a state suspected of the decreased production, respectively. Thus, discrimination of thrombocytopenia is facilitated by using support information for supporting the discrimination, the information considering not only analysis data on platelets but also analysis data on red blood cells and white blood cells.

Furthermore, presenting a physician with both the increased destruction score and the decreased production score facilitates discrimination by the physician in comparison with a case of presenting one of the scores.

6.4 Generation of Erythropenia Discrimination Support Information

Increased destruction score generator 58a and decreased production score generator 58b described above are capable of not only generating information for supporting discrimination of thrombocytopenia but also generating information for supporting discrimination of erythropenia (increased red-blood-cell destruction score and decreased red-blood-cell production score).

The procedure to generate scores of increased destruction and decreased production of red blood cells is the same as that for platelets illustrated in FIG. 9. "Platelet" in FIG. 9 should be replaced with "red blood cell."

Specific process procedures to generate scores of increased destruction and decreased production of red blood cells are as follows.

First, increased destruction score generator 58a selects analysis data (first target analysis data) used to generate discrimination support information on increased red-blood-cell destruction (first cause information) among the analysis data stored in analysis data storage 54c, by referring to increased destruction scoring information 54d-3 illustrated in FIG. 12 (Step S11).

Set in increased red-blood-cell destruction scoring information 54d-3 are first target analysis data on increased red-blood-cell destruction including: mean corpuscular volume (MCV), the number of neutrophils (Neut#), the number of reticulocytes (RET#), the number of platelets (PLT), and fragmented red-blood-cell indicator (FRC#). Increased destruction score generator 58a reads these first target analysis data from analysis data storage 54c.

Similarly, decreased production score generator 58b selects analysis data (second target analysis data) used to generate discrimination support information on decreased red-blood-cell production (second cause information) among the analysis data stored in analysis data storage 54c, by referring to decreased production scoring information 54d-4 illustrated in FIG. 13 (Step S11).

Set in decreased red-blood-cell production scoring information 54d-4 are second target analysis data on decreased red-blood-cell production including: the number of neutrophils (Neut#), the number of red blood cells (RBC#), the number of platelets (PLT), the number of reticulocytes (RET#), mean corpuscular volume (MCV), and red blood cell distribution width (RDW-SD). Decreased production score generator 58b reads these second target analysis data from analysis data storage 54c.

Subsequently, increased destruction score generator 58a scores (normalizes) values of first target analysis data according to increased red-blood-cell destruction scoring information (table illustrating values of measurement ranges) 54d-3 illustrated in FIG. 12.

Increased red-blood-cell destruction scoring information (table illustrating values of measurement ranges) 54d-3 defines correspondences between values of first target analysis data and scores (0 to 3). Increased destruction score generator 58a converts the value of each first target analysis data into a score (first score) according to scoring information 54d-3 (Step S12).

Similarly, decreased production score generator 58b scores (normalizes) values of second target analysis data according to decreased red-blood-cell production scoring information (table illustrating values of measurement ranges) 54d-4 illustrated in FIG. 13.

Decreased red-blood-cell production scoring information (table illustrating values of measurement ranges) 54d-4 also defines correspondences between values of second target analysis data and scores (0 to 3). Decreased production score generator 58b converts the value of each second target analysis data into a score (second score) according to scoring information 54d-4 (Step S12).

Then, increased destruction score generator 58a calculates an increased destruction score, using the first scores of the first target analysis data (Step S13).

Similarly, decreased production score generator 58b calculates a decreased production score, using the second scores of the second target analysis data (Step S13).

According to the above-described calculation formula, if the first target analysis data on the increased destruction are as illustrated in FIG. 12, the increased destruction score of red blood cells is obtained according to the following calculation formula. Note that no special condition is considered here, but a special condition may be considered as in the case of platelets.

$$B_{all}=[\text{score of mean corpuscular volume (MCV)} \times 2] + [\text{score of the number of neutrophils (Neut\#)} \times 1] + [\text{score of the number of reticulocytes (RET\#)} \times 3] + [\text{score of the number of platelets (PLT)} \times 1] + [\text{score of fragmented red-blood-cell indicator (FRC\#)} \times 2]$$

Increased destruction score of red blood cells$=B_{all} \div 5$

Moreover, if the second target analysis data on the decreased production are as illustrated in FIG. 13, the decreased production score of red blood cells is obtained according to the following calculation formula. Note that no special condition is considered here, but a special condition may be considered as in the case of platelets.

$B_{all}$=[score of the number of neutrophils (Neut#)× 1]+[score of the number of red blood cells (RBC#)×1.5]+[score of the number of platelets (PLT)×1.2]+[score of the number of reticulocytes (RET#)×3]+[score of mean corpuscular volume (MCV)×2]+[score of red blood cell distribution width (RDW-SD)×1]

Decreased production score of red blood cells=$B_{all}$÷6

Support information storage 54e of hard disk 51d stores, as support information, the increased destruction score and the decreased production score of red blood cells calculated as described above (Step S14).

7. Output of Support Information

FIGS. 14A to 15B illustrate output examples of support information outputted to display unit (output unit) 52 in information output step S5 of FIG. 5. FIG. 14A illustrates an example of displaying an increased platelet destruction score (platelet reduction/increased destruction suspect score) as first cause information and a decreased platelet production score (platelet reduction/decreased production suspect score) as second cause information respectively in graphs (bar graphs).

When scores (increased destruction score and decreased production score) are calculated in support information generation step S4, a score outputted in output step S5 may be only the larger (largest) score. However, outputting both of the calculated scores as illustrated in FIG. 14A facilitates discrimination. For example, suppose a case where an increased destruction score is 50 out of 100 and a decreased production score is 20 out of 100. In this case, outputting the increased destruction score of 50 and also displaying the decreased production score of 20 more strongly suggest not a decreased production state but an increased destruction state. Thus, displaying scores in such a comparable manner facilitates the discrimination. Note that the comparison of scores is facilitated by, for example, outputting the scores simultaneously on display unit (output unit) 52 to display both of the scores on display unit 52.

FIG. 14B illustrates an output example of support information in a case where the support information is constituted of the ITP suspect score (information indicating an ITP suspected state) as first cause information, an MDS suspect score (information indicating an MDS suspected state) as second cause information, and an AA suspect score (information indicating an AA suspected state) as third cause information.

Note that the ITP suspect score can be calculated similarly to the increased platelet destruction score. The MDS suspect score can be calculated by using the above-described calculation formula for the decreased platelet production score, the calculation formula having been modified, for example, by increasing the weight of analysis data strongly characterizing MDS. Similarly, the AA suspect score can be calculated by using the above-described calculation formula for the decreased platelet production score, the calculation formula having been modified, for example, by increasing the weight of analysis data strongly characterizing AA.

Figure 15A:
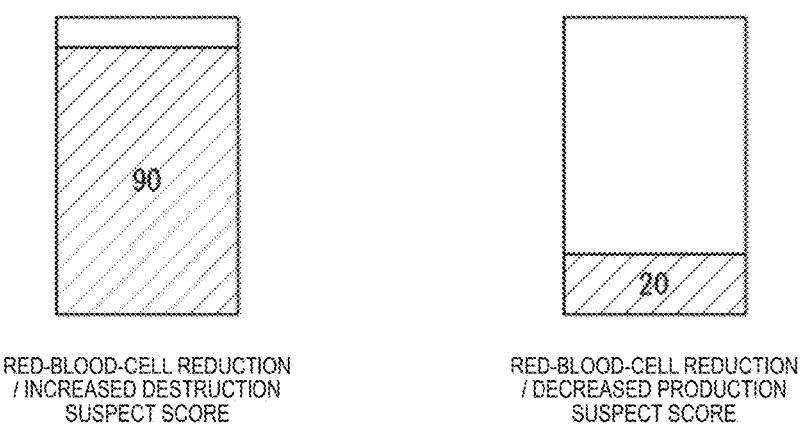
FIGS. 15A and 15B illustrate output examples of discrimination support information on erythropenia.

FIG. 15A illustrates an example of displaying an increased red-blood-cell destruction score (red-blood-cell reduction/increased destruction suspect score) as first cause information and a decreased red-blood-cell production score (red-blood-cell reduction/decreased production suspect score) as second cause information respectively in graphs (bar graphs). Note that, in FIG. 15A also, any one of the scores may be outputted, but outputting both of the scores facilitates the discrimination.

Figure 15B:
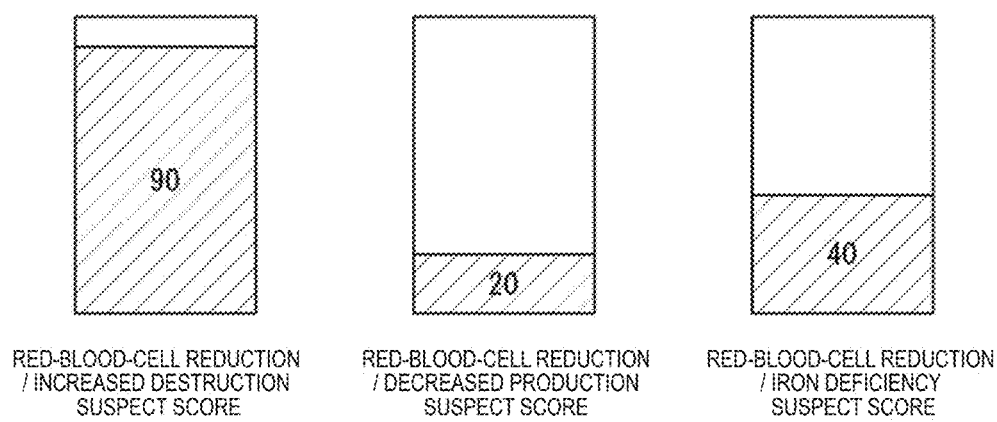

FIG. 15B illustrates an output example of support information in a case where the support information includes a red-blood-cell reduction/iron deficiency suspect score in addition to the red-blood-cell reduction/increased destruction suspect score and the red-blood-cell reduction/decreased production suspect score.

Note that the red-blood-cell reduction/iron deficiency suspect score can be calculated by using the above-described calculation formula for the decreased red-blood-cell production score, the calculation formula having been modified, for example, by increasing the weight of analysis data strongly characterizing iron deficiency.

When scores are displayed as in FIGS. 14A to 15B, a message may be outputted, depending on the scores, to urge the next test. Examples of the message used include "please measure ○○," "please check xx," "please check □□ in the ΔΔ test," and the like.

Figure 16:
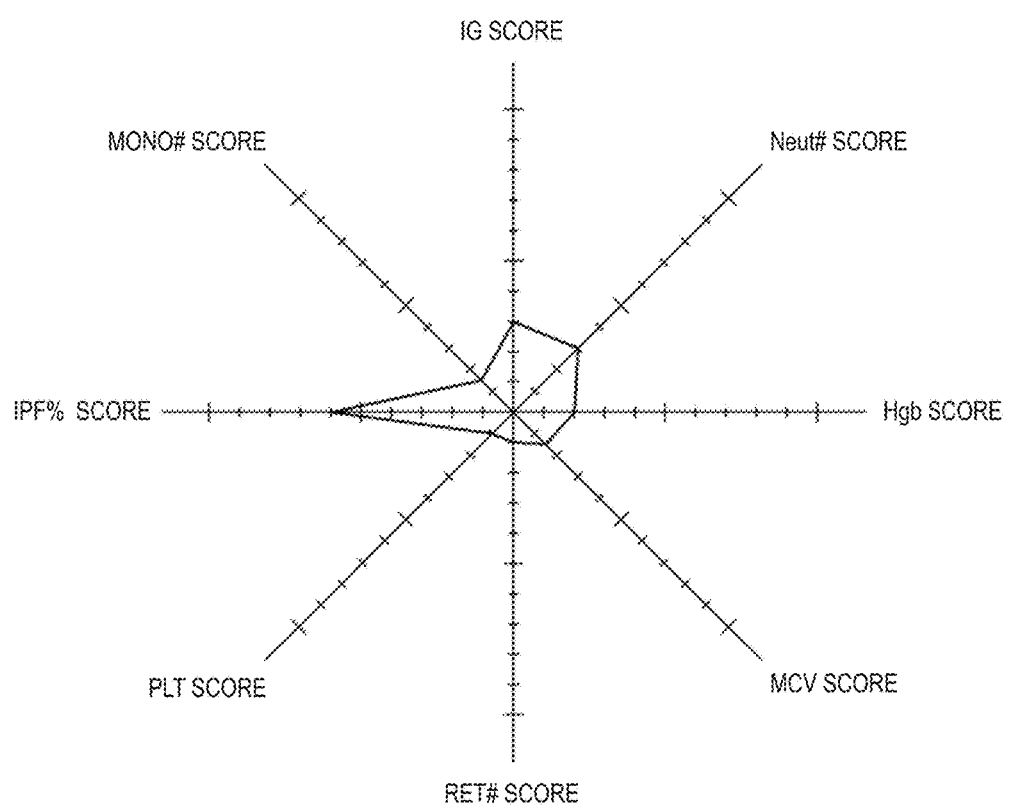
FIG. 16 is a chart for illustrating another output example of support information.

Furthermore, the mode of outputting support information is not limited to the outputting in the form of bar graph illustrating a value of a score obtained according to a calculation formula as in FIGS. 14A to 15B. Support information may be outputted in other graphic types such as radar chart as illustrated in FIG. 16. The radar chart in FIG. 16 sets each score of analysis data as a value on the corresponding axis. The radar chart displays scores of analysis data (or weighted scores of the analysis data). In this case, the size of the area of a portion surrounded in the radar chart corresponds to a score such as an increased destruction score obtained according to the calculation formula for the increased destruction score.

The modes for outputting support information illustrated in FIGS. 14A to 16 are merely examples, and various other modes can be employed.

As has been described above, the present embodiment makes it possible to improve the precision of information for supporting discrimination of a cause of a reduction in the number of blood cells.

Note that the invention is not limited to the above-described embodiment and modification examples, and can be modified in various manners.

The invention claimed is:

1. A blood cell analyzer comprising:
 a detector;
 a display;
 a memory; and
 a processor coupled to the detector, the display and the memory, wherein:
  the detector is communicatively coupled to the processor, the detector measuring blood cells contained in a blood sample and outputting measurement data of the blood sample based on the measured blood cells in the blood sample;
  the memory stores an idiopathic thrombocytopenic purpura discrimination support program; and the processor executes the idiopathic thrombocytopenic purpura diagnosis discrimination support program to perform operations comprising:
   analyzing the measurement data of the blood sample, outputted from the detector to produce a count of a number of platelets and a number of immature platelets, and hemoglobin data, generating analysis data including an immature platelet fraction from the count of the number of platelets and the number of immature platelets, and a hemoglobin concentration from the hemoglobin data produced based on analyzing the measurement data of the blood sample, generating support information for discriminating idiopathic thrombocytopenic purpura from aplastic anemia and myelodysplastic syndrome by using the analysis data including the immature platelet fraction and the hemoglobin concentration to improve the precision of the support information; and outputting the generated support information on the display including the immature platelet fraction and the hemoglobin concentration so as to facilitate a discrimination of idiopathic thrombocytopenic purpura from aplastic anemia and myelodysplastic syndrome based on the improved precision of the support information.

2. The blood cell analyzer according to claim 1, wherein the support information includes information on increased destruction of platelets.

3. The blood cell analyzer according to claim 2, wherein the analysis data further includes the number of neutrophils and the number of monocytes, and the operation of generating support information is performed by generating the support information by using the immature platelet fraction, the hemoglobin concentration, the number of neutrophils and the number of monocytes.

4. The blood cell analyzer according to claim 3, wherein the analysis data further includes at least one selected from an immature granulocyte fraction, a mean corpuscular volume, the number of reticulocytes and the number of platelets, and the operation of generating support information is performed by generating the support information by using the immature platelet fraction, the hemoglobin concentration, the number of neutrophils, the number of monocytes and at least one selected from the immature granulocyte fraction, the mean corpuscular volume, the number of reticulocytes and the number of platelets.

5. The blood cell analyzer according to claim 3, wherein the analysis data further includes an immature granulocyte fraction, a mean corpuscular volume, the number of reticulocytes and the number of platelets, and the processor is configured to perform operations such that generating support information is performed by integrating the immature platelet fraction, the hemoglobin concentration, the number of neutrophils, the number of monocytes, the immature granulocyte fraction, the mean corpuscular volume, the number of reticulocytes and the number of platelets.

6. The blood cell analyzer according to claim 5, wherein the processor is configured to perform operations further comprising generating scores of the immature platelet fraction, the hemoglobin concentration, the number of neutrophils, the number of monocytes, the immature granulocyte fraction, the mean corpuscular volume, the number of reticulocytes and the number of platelets respectively, and the processor is configured to perform operations such that generating support information is performed based on the generated scores of the immature platelet fraction, the hemoglobin concentration, the number of neutrophils, the number of monocytes, the immature granulocyte fraction, the mean corpuscular volume, the number of reticulocytes and the number of platelets.

7. The blood cell analyzer according to claim 3, wherein the processor is configured to perform operations further comprising generating scores of the immature platelet fraction, the hemoglobin concentration, the number of neutrophils and the number of monocytes respectively, and the processor is configured to perform operations such that generating support information is performed based on the generated scores of the immature platelet fraction, the hemoglobin concentration, the number of neutrophils and the number of monocytes.

8. The blood cell analyzer according to claim 7, wherein the processor is configured to perform operations further comprising assigning weights to respective ones of the scores, and, the processor is configured to perform operations such that generating support information based on the weighted scores.

9. The blood cell analyzer according to claim 1, wherein the analysis data further includes at least one selected from an immature granulocyte fraction, a mean corpuscular volume, the number of reticulocytes and the number of platelets, and the operation of generating support information is performed by generating the support information by using the immature platelet fraction, the hemoglobin concentration, and at least one selected from the immature granulocyte fraction, the mean corpuscular volume, the number of reticulocytes and the number of platelets.

10. The blood cell analyzer according to claim 1, wherein the processor is configured to perform operations further comprising generating scores of the immature platelet fraction and the hemoglobin concentration respectively, and the processor is configured to perform operations such that generating support information is performed based on the generated scores of the immature platelet fraction and the hemoglobin concentration.

11. A system for providing a physician with support information for discriminating idiopathic thrombocytopenic purpura from aplastic anemia and myelodysplastic syndrome, comprising a blood cell analyzer, wherein the blood cell analyzer produces analysis data including an immature platelet fraction and a hemoglobin concentration from measurement data of blood cells contained in a blood sample;

a display;

a memory; and a processor coupled to the memory, the display and the blood cell analyzer, wherein the memory stores an idiopathic thrombocytopenic purpura discrimination support program; and the processor executes the idiopathic thrombocytopenic purpura discrimination support program to perform operations comprising:

receiving the analysis data including the immature platelet fraction and the hemoglobin concentration from the blood cell analyzer, generating support information for discriminating idiopathic thrombocytopenic purpura from aplastic anemia and myelodysplastic syndrome by using the analysis data including the immature platelet fraction and the hemoglobin concentration to improve the precision of the support information; and outputting the generated support information on the display including the immature platelet fraction and the hemoglobin concentration so as to facilitate a discrimination of idiopathic thrombocytopenic purpura from aplastic anemia and myelodysplastic syndrome based on the improved precision of the support information.

12. The system according to claim 11, wherein
the analysis data further includes the number of neutrophils and the number of monocytes, and
the processor is configured to perform operations such that generating support information is performed based on the immature platelet fraction, the hemoglobin concentration, the number of neutrophils and the number of monocytes.

13. The system according to claim 12, wherein
the analysis data further includes an immature granulocyte fraction, a mean corpuscular volume, the number of reticulocytes and the number of platelets, and
the processor is configured to perform operations such that generating support information is performed based on the immature platelet fraction, the hemoglobin concentration, the number of neutrophils, the number of monocytes, the immature granulocyte fraction, the mean corpuscular volume, the number of reticulocytes and the number of platelets.

14. The system according to claim 12, wherein
the processor is configured to perform operations further comprising generating scores of the immature platelet fraction, the hemoglobin concentration, the number of neutrophils and the number of monocytes respectively, and
the processor is configured to perform operations such that generating support information is performed based on the scores of the immature platelet fraction, the hemoglobin concentration, the number of neutrophils and the number of monocytes.

15. The system according to claim 11, wherein
the processor is configured to perform operations further comprising generating scores of the immature platelet fraction and the hemoglobin concentration respectively, and
the processor is configured to perform operations such that generating support information is performed based on the scores of the immature platelet fraction and the hemoglobin concentration.

16. A computer-implemented method for facilitating discrimination of idiopathic thrombocytopenic purpura from aplastic anemia and myelodysplastic syndrome, comprising
receiving, in a processor, analysis data of blood cells contained in a blood sample from a blood cell analyzer, the analysis data including an immature platelet fraction and a hemoglobin concentration, and generating, in the processor, support information for discriminating idiopathic thrombocytopenic purpura from aplastic anemia and myelodysplastic syndrome by using the analysis data including the immature platelet fraction and the hemoglobin concentration to improve the precision of the support information; and outputting, by the processor, the generated support information on a display including the immature platelet fraction and the hemoglobin concentration so as to facilitate a discrimination of idiopathic thrombocytopenic purpura from aplastic anemia and myelodysplastic syndrome based on the improved precision of the support information.

17. The method according to claim 16, wherein
the analysis data further includes the number of neutrophils and the number of monocytes, and
generating support information is performed based on the immature platelet fraction, the hemoglobin concentration, the number of neutrophils and the number of monocytes.

18. The method according to claim 17, wherein
the analysis data further includes an immature granulocyte fraction, a mean corpuscular volume, the number of reticulocytes and the number of platelets, and
generating support information is performed by generating the support information based on the immature platelet fraction, the hemoglobin concentration, the number of neutrophils, the number of monocytes, the immature granulocyte fraction, the mean corpuscular volume, the number of reticulocytes and the number of platelets.

19. The method according to claim 17, further comprising:
generating scores of the immature platelet fraction, the hemoglobin concentration, the number of neutrophils and the number of monocytes respectively,
wherein generating support information is performed by generating the support information based on the scores of the immature platelet fraction, the hemoglobin concentration, the number of neutrophils and the number of monocytes.

20. The method according to claim 16, further comprising:
generating scores of the immature platelet fraction and the hemoglobin concentration respectively,
wherein generating support information is performed by generating the support information based on the scores of the immature platelet fraction and the hemoglobin concentration.

* * * * *